United States Patent
Ranucci et al.

(10) Patent No.: US 6,695,782 B2
(45) Date of Patent: *Feb. 24, 2004

(54) ULTRASONIC PROBE DEVICE WITH RAPID ATTACHMENT AND DETACHMENT MEANS

(75) Inventors: Kevin Ranucci, Coventry, RI (US); Robert A. Rabiner, North Reading, MA (US); Bradley A. Hare, Chelmsford, MA (US); Mark J. Varady, Holliston, MA (US); Rebecca I. Marciante, North Reading, MA (US); Roy Robertson, Ipswich, MA (US)

(73) Assignee: OmniSonics Medical Technologies, Inc., Wilmington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/975,725

(22) Filed: Oct. 11, 2001

(65) Prior Publication Data

US 2002/0055754 A1 May 9, 2002

Related U.S. Application Data

(63) Continuation-in-part of application No. 09/625,803, filed on Jul. 26, 2000.
(60) Provisional application No. 60/157,824, filed on Oct. 5, 1999, and provisional application No. 60/225,060, filed on Aug. 14, 2000.

(51) Int. Cl.[7] .................................................. A61N 7/00
(52) U.S. Cl. ............................. 600/439; 601/4; 604/22
(58) Field of Search ................................ 600/104, 121, 600/122, 123, 135, 139, 140, 141, 153, 154, 155, 156, 160–165, 437, 439; 601/2–4; 606/169, 46, 171, 180; 604/22

(56) References Cited

U.S. PATENT DOCUMENTS

| | | | | |
|---|---|---|---|---|
| 2,990,616 A | 7/1961 | Balamuth et al. | ............ | 433/119 |
| 3,526,219 A | 9/1970 | Balamuth | .................... | 600/565 |
| 3,565,062 A | 2/1971 | Kuris | .......................... | 606/169 |

(List continued on next page.)

FOREIGN PATENT DOCUMENTS

| | | | | |
|---|---|---|---|---|
| EP | 0293472 | 12/1988 | ........... | A61B/17/22 |
| EP | 0493047 A1 | 1/1992 | | |
| EP | 0541249 | 5/1993 | ........... | A61F/9/007 |

(List continued on next page.)

*Primary Examiner*—Eleni Mantis Mercader
(74) *Attorney, Agent, or Firm*—Palmer & Dodge, LLP; Richard B. Smith; David J. Dykeman

(57) ABSTRACT

An ultrasonic tissue ablation device comprising a transversely vibrating elongated probe, and a coupling assembly for probe attachment detachment that enables the probe assembly and separation from the device body that includes the ultrasound energy source and a sound conductor, and a method of use for removal of vascular occlusions in blood vessels. The coupling assembly enables incorporation of elongated probes with small cross sectional lumens such as a catheter guidewires. The probe detachability allows insertion manipulation and withdrawal independently of the device body. The probe can be used with acoustic and/or aspirations sheaths to enhance destruction and removal of an occlusion. The horn assembly of the device that contains a sound conducting horn functions as an energy regulator and reservoir for the probe, and precludes loss of probe cavitation energy by its bending or damping within the blood vessel.

68 Claims, 13 Drawing Sheets

U.S. PATENT DOCUMENTS

| | | | |
|---|---|---|---|
| 3,589,363 A | 6/1971 | Banko | 604/22 |
| 3,805,787 A | 4/1974 | Banko | 128/276 |
| 3,861,391 A | 1/1975 | Antonevich et al. | 606/128 |
| 4,136,700 A | 1/1979 | Broadwin et al. | 606/169 |
| 4,236,510 A | 12/1980 | Hatter et al. | 601/2 |
| 4,474,180 A | 10/1984 | Angulo | 128/328 |
| 4,486,680 A | 12/1984 | Bonnet et al. | 310/323.19 |
| 4,493,694 A | 1/1985 | Wuchinich | 604/22 |
| 4,504,264 A | 3/1985 | Kelman | 604/22 |
| 4,526,571 A | 7/1985 | Wuchinich | 604/22 |
| 4,535,759 A | 8/1985 | Polk et al. | 128/24 A |
| 4,634,420 A | 1/1987 | Spinosa et al. | 604/22 |
| 4,838,853 A | 6/1989 | Parisi | 604/22 |
| 4,867,141 A | 9/1989 | Nakada et al. | 601/4 |
| 4,870,953 A | 10/1989 | DonMicheal et al. | 128/24 A |
| 4,886,491 A | 12/1989 | Parisi et al. | 604/22 |
| 4,920,954 A | 5/1990 | Alliger et al. | 128/24 |
| 4,922,902 A | 5/1990 | Wuchinich et al. | 604/22 |
| 4,931,047 A | 6/1990 | Broadwin et al. | 604/22 |
| 4,961,424 A | 10/1990 | Bubota et al. | 128/24 |
| 4,962,755 A | 10/1990 | King et al. | 601/2 |
| 4,989,583 A | 2/1991 | Hood | 128/24 |
| 5,015,221 A | 5/1991 | Smith | 475/19 |
| 5,015,227 A | 5/1991 | Broadwin et al. | 604/22 |
| 5,026,387 A | 6/1991 | Thomas | 606/169 |
| 5,057,119 A | 10/1991 | Clark et al. | 606/169 |
| 5,057,182 A | 10/1991 | Wuchinich | 156/580.1 |
| 5,058,570 A | 10/1991 | Idemoto et al. | 128/24 AA |
| 5,059,210 A | 10/1991 | Clark et al. | 606/169 |
| 5,062,827 A | 11/1991 | Wiksell | 604/22 |
| 5,112,300 A | 5/1992 | Ureche | 604/22 |
| 5,116,343 A | 5/1992 | Ams et al. | 606/128 |
| 5,123,903 A * | 6/1992 | Quaid et al. | 604/22 |
| 5,163,421 A | 11/1992 | Bernstein et al. | 128/24.1 |
| 5,167,619 A | 12/1992 | Wuchinich | 604/22 |
| 5,171,387 A | 12/1992 | Wuchinich | 156/73.3 |
| 5,176,677 A | 1/1993 | Wuchinich | 604/356 |
| 5,180,363 A | 1/1993 | Idemoto et al. | 202/32 |
| 5,190,517 A | 3/1993 | Zieve et al. | 604/22 |
| 5,221,282 A | 6/1993 | Wuchinich | 606/99 |
| 5,243,997 A | 9/1993 | Uflacker et al. | 600/565 |
| 5,255,669 A * | 10/1993 | Kubota et al. | 601/3 |
| 5,267,954 A | 12/1993 | Nita | 604/22 |
| 5,269,297 A | 12/1993 | Weng et al. | 128/24 |
| 5,271,735 A | 12/1993 | Greenfeld et al. | 604/266 |
| 5,300,021 A | 4/1994 | Wuchinich | 604/22 |
| 5,304,115 A | 4/1994 | Pflueger et al. | 604/22 |
| 5,312,328 A | 5/1994 | Nita et al. | 604/22 |
| 5,312,329 A | 5/1994 | Beaty et al. | 604/22 |
| 5,324,299 A | 6/1994 | Davison et al. | 606/167 |
| 5,334,183 A | 8/1994 | Wuchinich | 606/46 |
| 5,342,292 A | 8/1994 | Nita et al. | 604/22 |
| 5,358,505 A | 10/1994 | Wuchinich | 606/99 |
| 5,366,490 A | 11/1994 | Edwards et al. | 607/99 |
| 5,368,558 A | 11/1994 | Nita | 604/22 |
| 5,380,274 A | 1/1995 | Nita | 604/22 |
| 5,382,228 A | 1/1995 | Nita et al. | 604/22 |
| 5,391,144 A * | 2/1995 | Sakurai et al. | 604/22 |
| 5,397,293 A | 3/1995 | Alliger et al. | 601/2 |
| 5,397,301 A | 3/1995 | Pflueger et al. | 604/22 |
| 5,405,318 A | 4/1995 | Nita | 604/22 |
| 5,417,654 A | 5/1995 | Kelman | 604/22 |
| 5,417,672 A | 5/1995 | Nita et al. | 604/353 |
| 5,419,761 A | 5/1995 | Narayanan et al. | 604/22 |
| 5,427,118 A | 6/1995 | Nita et al. | 128/772 |
| 5,447,509 A | 9/1995 | Mills et al. | 606/1 |
| 5,458,612 A | 10/1995 | Chin | 606/192 |
| 5,469,853 A | 11/1995 | Law et al. | 128/662.06 |
| 5,472,441 A | 12/1995 | Edwards et al. | 606/41 |
| 5,484,398 A | 1/1996 | Stoddard | 604/22 |
| 5,498,236 A | 3/1996 | Dubrul et al. | 604/22 |
| 5,507,738 A * | 4/1996 | Ciervo | 606/1 |
| 5,516,043 A | 5/1996 | Manna et al. | 239/102.2 |
| 5,524,635 A * | 6/1996 | Uflacker et al. | 600/585 |
| 5,628,743 A | 5/1997 | Cimino | 606/1 |
| 5,630,837 A | 5/1997 | Crowley | 601/2 |
| 5,672,172 A | 9/1997 | Zupkas | 606/20 |
| 5,676,649 A | 10/1997 | Boukhny et al. | 604/22 |
| 5,713,848 A | 2/1998 | Dubrul et al. | 604/22 |
| 5,720,710 A | 2/1998 | Tachibana et al. | 601/2 |
| 5,725,494 A | 3/1998 | Brisken | 604/22 |
| 5,728,062 A | 3/1998 | Brisken | 604/22 |
| 5,735,811 A | 4/1998 | Brisken | 604/22 |
| 5,741,225 A | 4/1998 | Lax et al. | 604/22 |
| 5,772,627 A | 6/1998 | Acosta et al. | 604/22 |
| 5,827,203 A | 10/1998 | Nita | 601/2 |
| 5,836,896 A | 11/1998 | Rosenschein | 601/2 |
| 5,843,017 A | 12/1998 | Yoon | 604/22 |
| 5,846,218 A | 12/1998 | Brisken et al. | 604/22 |
| 5,895,370 A | 4/1999 | Edwards et al. | 604/22 |
| 5,931,805 A | 8/1999 | Brisken | 604/22 |
| 5,935,096 A | 8/1999 | Barrett | 604/22 |
| 5,935,142 A | 8/1999 | Hood | 606/169 |
| 5,957,882 A | 9/1999 | Nita et al. | 604/22 |
| 5,964,756 A | 10/1999 | McGaffigan et al. | 606/41 |
| 5,971,949 A * | 10/1999 | Levin et al. | 604/22 |
| 5,989,208 A | 11/1999 | Nita | 604/22 |
| 5,989,209 A | 11/1999 | Barrett | 604/22 |
| 5,989,274 A | 11/1999 | Davison et al. | 606/169 |
| 6,032,078 A | 2/2000 | Rudie | 607/101 |
| 6,033,375 A | 3/2000 | Brumbach | 604/22 |
| 6,224,565 B1 | 5/2001 | Cimino | 604/22 |
| 6,524,251 B2 * | 2/2003 | Rabiner et al. | 600/439 |
| 2002/0077550 A1 * | 6/2002 | Rabiner et al. | 600/439 |
| 2002/0077643 A1 * | 6/2002 | Rabiner et al. | 606/169 |
| 2002/0107446 A1 * | 8/2002 | Rabiner et al. | 600/439 |

FOREIGN PATENT DOCUMENTS

| | | | |
|---|---|---|---|
| WO | WO 90/01300 | 2/1990 | A61B/17/32 |
| WO | WO 95/03740 | 2/1995 | A61B/17/20 |
| WO | WO 96/07377 | 3/1996 | A61F/9/007 |
| WO | WO 98/35721 | 8/1998 | A61B/17/22 |
| WO | WO 98/55032 | 12/1998 | A61B/17/22 |
| WO | WO 99/33404 | 7/1999 | A61F/9/007 |
| WO | WO 99/35982 | 7/1999 | A61B/17/32 |
| WO | WO 00/21444 | 4/2000 | A61B/17/20 |

* cited by examiner

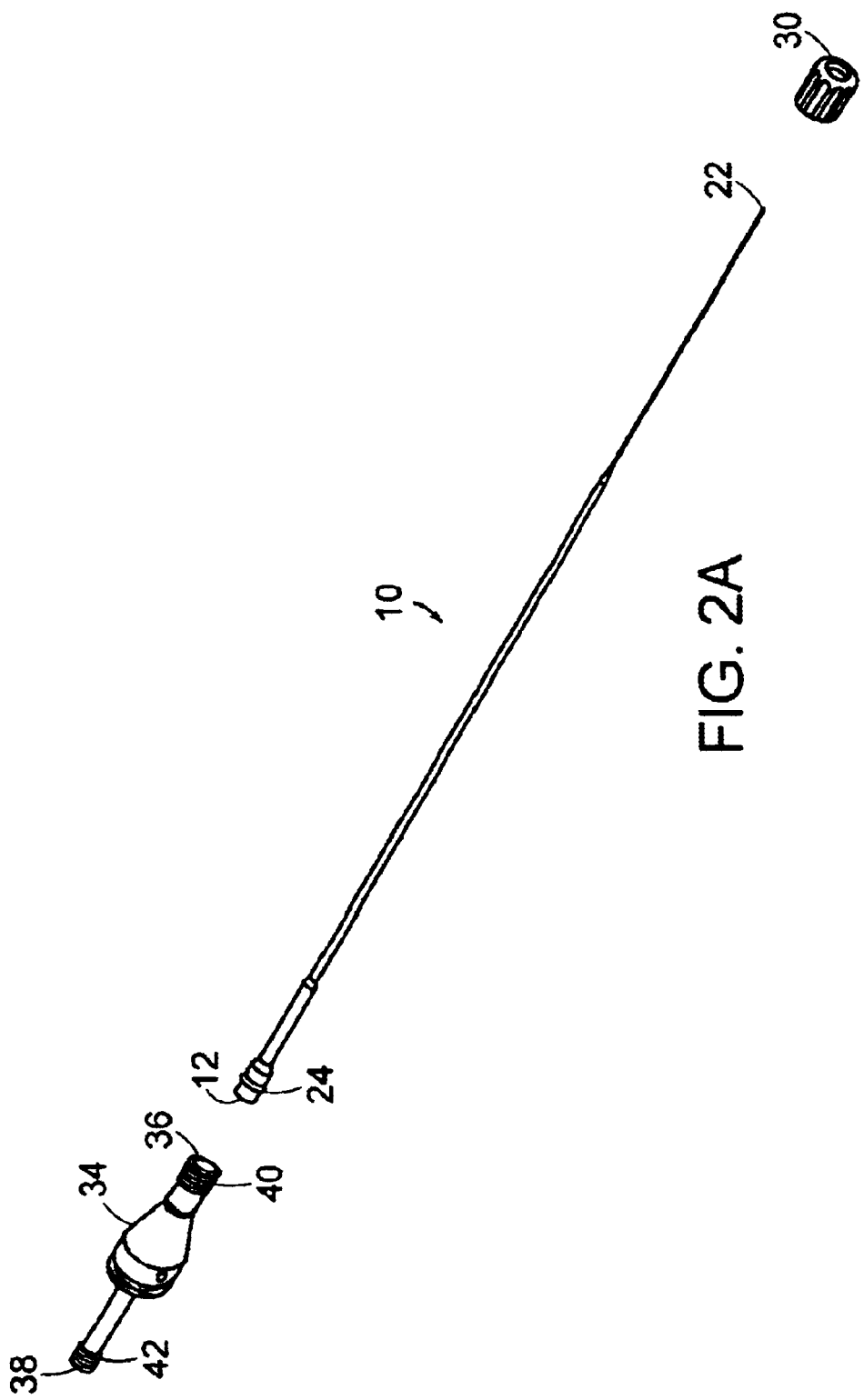

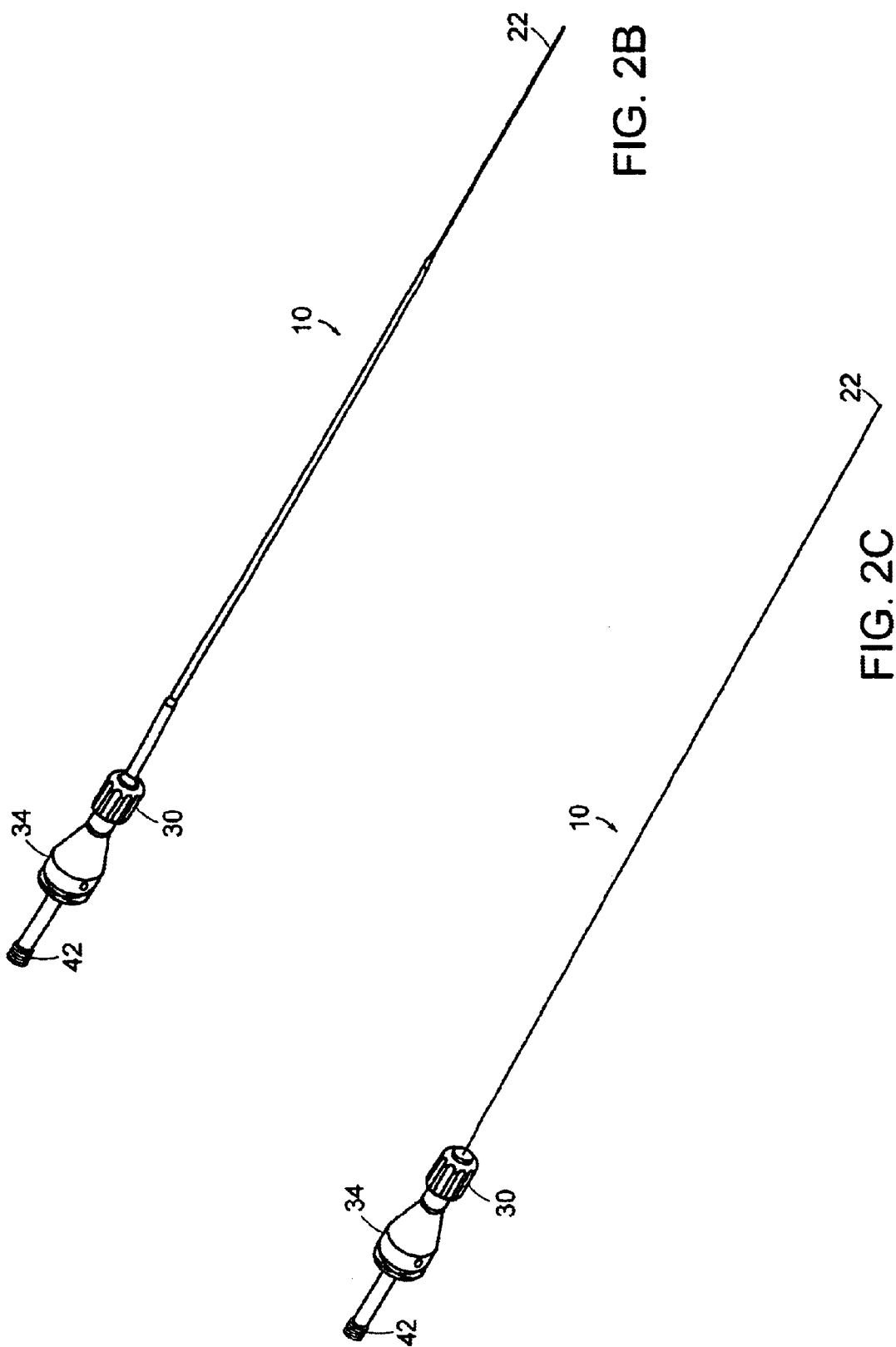

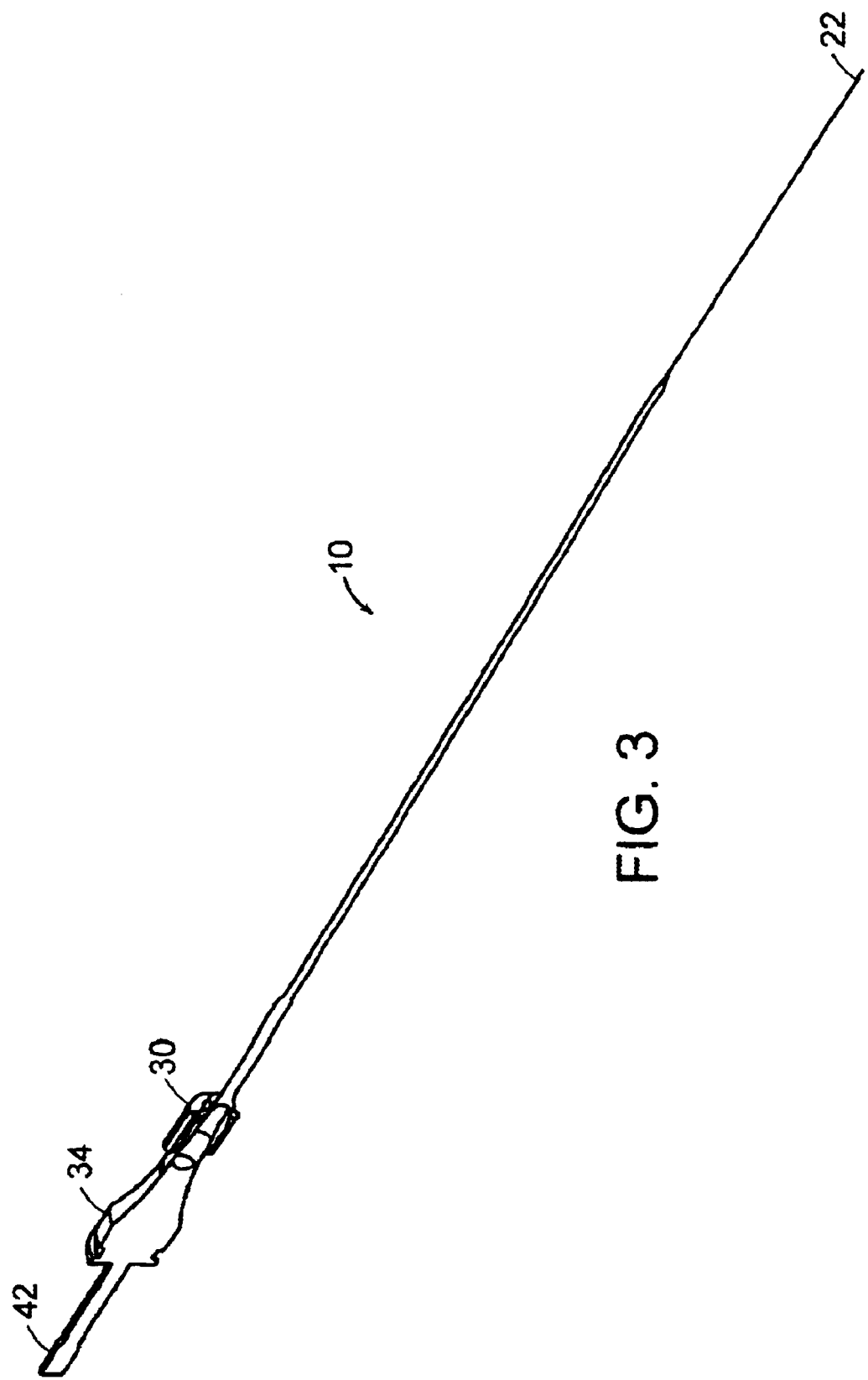

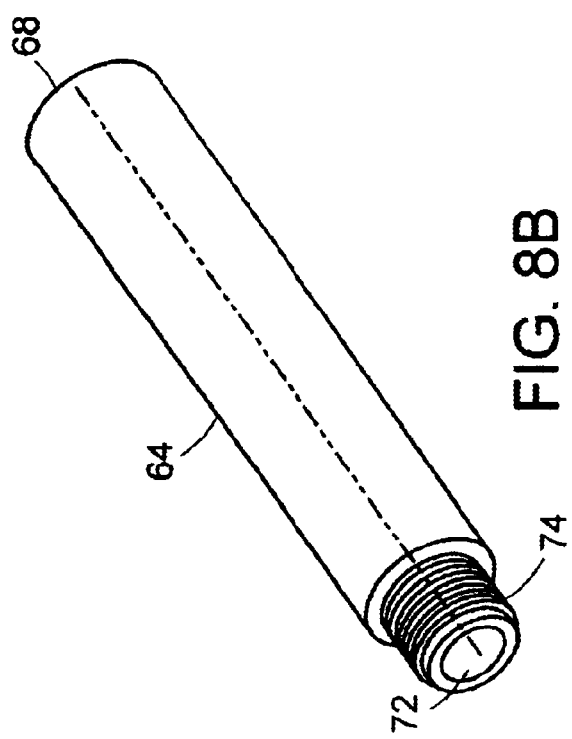
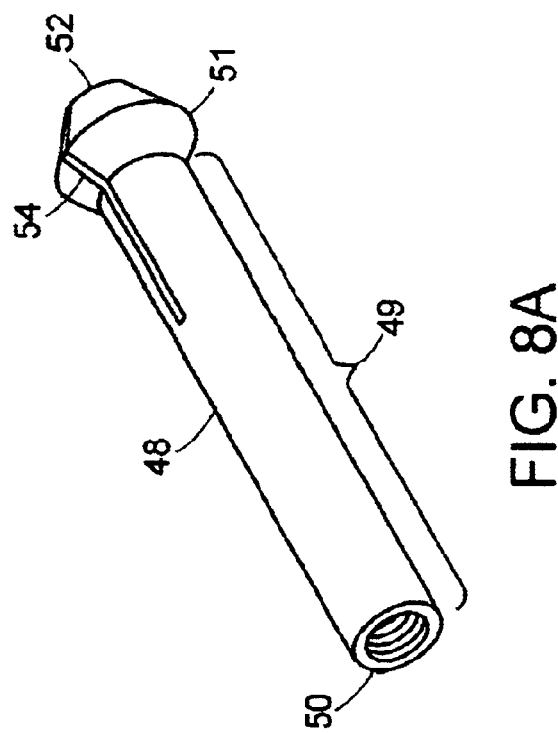

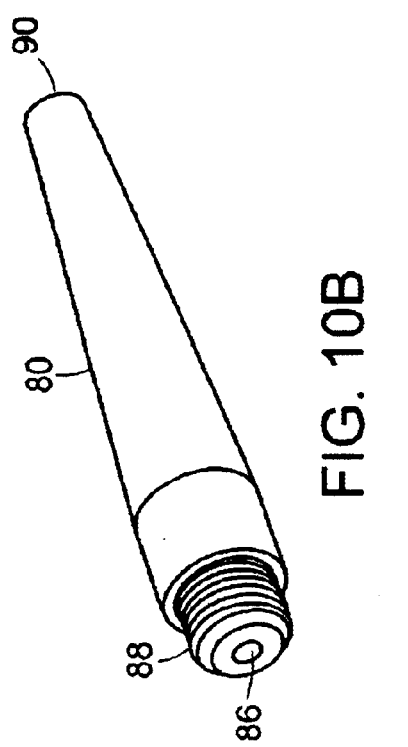
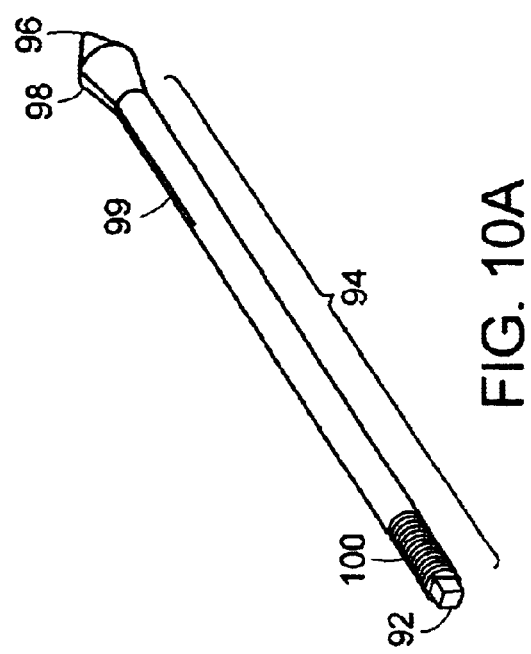
FIG. 10B
FIG. 10A

ULTRASONIC PROBE DEVICE WITH RAPID ATTACHMENT AND DETACHMENT MEANS

RELATED APPLICATIONS

This application is a continuation in part of U.S. application Ser. No. 09/625,803 filed on Jul. 26, 2000 which claims priority to U.S. Provisional Application No. 60/157,824 filed on Oct. 5, 1999, and claims the benefit of U.S. Provisional Application No. 60/225,060 filed on Aug. 14, 2000, the entirety of which is incorporated herein by reference.

FIELD OF THE INVENTION

The present invention relates generally to medical devices, and more particularly to an apparatus and method for using an ultrasonic medical devices operating in a transverse mode emulsification of endovascular materials by causing tissue fragmentation of occlusion materials. The invention also relates to an apparatus emitting ultrasonic energy in transverse mode used in combination with an elongated flexible catheter wire, wherein the probe is rapidly attachable to and detachable from the ultrasonic energy source component of the device.

BACKGROUND OF THE INVENTION

Vascular occlusions (clots or thrombi and occlusional deposits, such as calcium, fatty deposits, or plaque) result in the restriction or blockage of blood flow in the vessels in which they occur. Occlusions result in oxygen deprivation ("ischemia") of tissues supplied by these blood vessels. Prolonged ischemia results in permanent damage of tissue that can lead to myocardial infarction, stroke, or death. Targets for occlusion include coronary arteries, peripheral arteries and other blood vessels. The disruption of an occlusion or thrombolysis can be effected by pharmacological agents and/or or mechanical means.

Ultrasonic probes are devices which use ultrasonic energy to fragment body tissue (see, e.g., U.S. Pat. Nos. 5,112,300; 5,180,363; 4,989,583; 4,931,047; 4,922,902; and 3,805,787) and have been used in many surgical procedures. The use of ultrasonic energy has been proposed both to mechanically disrupt clots, and to enhance the intravascular delivery of drugs to clot formations (see, e.g., U.S. Pat. Nos. 5,725,494; 5,728,062; and 5,735,811). Ultrasonic devices used for vascular treatments typically comprise an extra-corporeal transducer coupled to a solid metal wire that is attached to a plurality of wires at the distal end, that is then threaded through the blood vessel and placed in contact with the occlusion (see, e.g., U.S. Pat. No. 5,269,297). In some cases, the transducer is delivered to the site of the clot, the transducer comprising a bendable plate (see, U.S. Pat. No. 5,931,805).

The ultrasonic energy produced by an ultrasonic probe is in the form of very intense, high frequency sound vibrations that result in powerful chemical and physical reactions in the water molecules within a body tissue or surrounding fluids in proximity to the probe. These reactions ultimately result in a process called "cavitation," which can be thought of as a form of cold (i.e., non-thermal) boiling of the water in the body tissue, such that microscopic bubbles are rapidly created and destroyed in the water creating cavities in their wake. As surrounding water molecules rush in to fill the cavity created by collapsed bubbles, they collide with each other with great force. This process is called cavitation and results in shock waves running outward from the collapsed bubbles which can fragment or ablate material such as surrounding tissue in the vicinity of the probe.

Some ultrasonic probes include a mechanism for irrigating an area where the ultrasonic treatment is being performed (e.g., a body cavity or lumen) to wash tissue debris from the area. Mechanisms used for irrigation or aspiration described in the art are generally structured such that they increase the overall cross-sectional profile of the probe, by including inner and outer concentric lumens within the probe to provide irrigation and aspiration channels for removal of particulate matter. In addition to making the probe more invasive, prior art probes also maintain a strict orientation of the aspiration and the irrigation mechanism, such that the inner and outer lumens for irrigation and aspiration remain in a fixed position relative to one another, which is generally closely adjacent the area of treatment. Thus, the irrigation lumen does not extend beyond the suction lumen (i.e., there is no movement of the lumens relative to one another) and any aspiration is limited to picking up fluid and/or tissue remnants within the defined distance between the two lumens.

Another drawback of existing ultrasonic medical probes is that they typically remove tissue relatively slowly in comparison to instruments that excise tissue by mechanical cutting. Part of the reason for this is that existing ultrasonic devices rely on a longitudinal vibration of the tip of the probe for their tissue-disrupting effects. Because the tip of the probe is vibrated in a direction in line with the longitudinal axis of the probe, a tissue-destroying effect is only generated at the tip of the probe. One solution that has been proposed is to vibrate the tip of the probe in a direction other than perpendicular to the longitudinal axis of the probe, in addition to vibrating the tip in the longitudinal direction. It is proposed that such motions will supplement the main point of tissue destruction, which is at the probe tip, since efficiency is determined by surface area of the probe tip. For example, U.S. Pat. No. 4,961,424 to Kubota, et al. discloses an ultrasonic treatment device that produces both a primary longitudinal motion, and a supplementary lateral motion of the probe tip to increase the tissue disrupting efficiency. The Kubota, et al. device, however, still relies primarily on the tip of the probe to act as a working surface. The ancillary lateral motion of the probe is intended to provide an incremental efficiency for the device operation. Thus, while destruction of tissue in proximity to the tip of the probe is more efficient, tissue destruction is still predominantly limited to the area in the immediate vicinity at the tip of the probe. The said invention is therefore limited in its ability to ablate tissue within inner surfaces of cylindrical blood vessels, for example, in vascular occlusions. U.S. Pat. No. 4,504,264 to Kelman discloses an ultrasonic treatment device containing a probe that is capable of longitudinal vibrations and lateral oscillation. The said invention is intended to improve the efficiency of ultrasonic tissue removal by providing a dual function of a fragmentation and a cutting device. Tissue fragmentation is caused primarily by oscillating the tip of the probe in addition to relying on longitudinal vibrations of the probe, while the lateral oscillations. Tissue fragmentation is caused primarily at the tip of the device, while the oscillatory motion can be employed by the surgeon to cut tissue, thereby increasing efficiency of surgical procedures. The foregoing inventions also require complex instrument design that require incorporation of a plurality of electrodes, ultrasound frequency generating elements, switches or voltage controllers.

The longitudinal probe vibration required for tissue ablation in prior art devices necessitates the probe lengths to be relatively short, since use of long probes result in a substantial loss of ultrasonic energy at the probe tip due to thermal dissipation and undesirable horizontal vibration that interferes with the required longitudinal vibration.

Although narrow probe diameters are advantages especially for negotiation through narrow blood vessels and occluded arteries, the utilization of such probes have been precluded by inability to effectively control the vibrational amplitude of thin probes, that result in potential damage to the probe and greater risk of tissue damage resulting from their use. The use of narrow-diameter probes have been disclosed in the art for providing greater maneuverability ease of insertion in narrow blood vessels. U.S. Pat. No. 4,920,954 to Allinger discloses a narrow diameter ultrasonic device wherein a rigid sleeve is used to prevent transverse vibrations U.S. Pat. No. 5,380,274 discloses a narrow diameter probe for improved longitudinal vibration having a sheath to inhibit transverse vibration U.S. Pat. No. 5,469,853 to Law discloses a thin, longitudinally vibrating ultrasonic device with a bendable sheath that facilitates directing the probe within narrow blood vessels. While the prior art has focused on the need for using sheaths on thin ultrasonic devices, their use has been entirely to prevent transverse vibrations of the device and to protect such devices from damage resulting from such vibrations.

Based on the aforementioned limitations of ultrasonic probes in the art, there is a need for ultrasonic probe functioning in a transverse mode that further obviates the shortcomings of that further overcomes limitations imposed by of narrow diameter requirements for efficient operation of such probes for rapid tissue ablation. Transversely vibrating ultrasonic probes for tissue ablation are described in the Applicant's co-pending provisional applications U.S. Ser. Nos. 60/178,901 and 60/225,060, and 20563/1010 (Attorney Docket No.) which further describe the design parameters for such a probe its use in ultrasonic devices for tissue ablation. The entirety of these applications are herein incorporated by reference.

This limitation has precluded the use of ultrasonic tissue ablation devices in surgical procedures wherein access to vascular occlusion requires traversing an anatomically lengthy or sharply curved path along tubular vessels. The self-suggesting idea of effecting ultrasonic transmission through a plurality of flexible thin wires has been found impracticable because (1) relatively high power (~25 watts) is required to deliver sufficient energy to the probe tip, and (2) such thin wires tend to perform buckling vibrations, resulting in almost the entire ultrasonic power introduced in the probe is dissipated during its passage to the probe tip.

The relatively high-energy requirement for such devices causes probe heating that can cause fibrin to re-clot blood within the occluded vessel (thermally induced re-occlusion). Additionally, the elevation in probe temperature is not just limited to probe tip, but also occurs at points wherein the narrow diameter wire probes have to bend to conform to the shape of the blood vessel, thereby limiting causing probe damage and limiting its reuse.

A single thick wire probe on the other hand, cannot negotiate the anatomical curves of tubular arterial and venous vessels due to its inflexibility, and could cause damage to the interior wall of such vessels. Currently, such exchange procedures are not possible because ultrasonic probes used in endovascular procedures are permanently attached to the transducer energy source or a probe handle coupled to such source, such as for example, by welding, thereby precluding probe detachment. Moreover, since probe vibration in such devices in a longitudinal mode, i.e. along the probe longitudinal axis, a proximal contact with the transducer or the probe handle segment connect is essential to prevent a "hammering" effect that can result in probe damage.

SUMMARY OF THE INVENTION

The present invention relates to an ultrasonic device comprising an elongated catheter probe vibrating substantially in a direction transverse to the probe longitudinal axis and capable of emulsifying endovascular materials, particularly tissue. The diameter of the catheter probe is sufficiently small to confer flexibility on said probe so as to enable its negotiation through narrow and anatomically curved tubular vessels to the site of an occlusion that is remotely located from the point of probe insertion into the body. The catheter probe of the invention is designed to work in conjunction with standard vascular introducers and guide catheters. Another aspect of the invention is to provide a rapidly attachable and detachable or "quick attachment-detachment" means (referred to hereinafter as "QAD") for the catheter probe to and from the ultrasonic energy source, thereby enabling manipulation and positioning of the probe within the body vessel without being limited by the relatively bulky energy generating source. The catheter probe of the invention additionally comprises a concentric tubular sheath to facilitate fluid irrigation, aspiration of ablated tissue fragments and introducing a therapeutic drug to the site of occlusion.

An ultrasonic probe vibrating in a transverse mode for removal of occlusions in blood vessels has been disclosed in applicants' co-pending application Ser. No. 09/776,015, the entireity of which is incorporated herein as reference. The said reference discloses an ultrasonic device in which a transducer is connected to a probe with a flexible tip capable of vibrating in a direction transverse to the probe longitudinal axis. With such a probe a situation may arise where it will be desirable to utilize an elongated probe resembling a catheter guide-wire probe to make possible exchange procedures often used in angioplasty.

In general, it is an object of the invention to provide an ultrasonic medical device for removing vascular occlusions comprising a detachable elongated catheter guide wire probe capable of vibrating in a transverse mode.

Another object of the invention is to provide an elongated guide wire probe of the above character of the above character that is and comparable in size to existing guide wires.

Another object of the invention is to provide an elongated guide wire probe of the above character which includes a quick attachment-detachment means to an ultrasound energy source.

Another object of the invention is to provide an elongated guide wire probe of the above characteristics which is compatible with the existing guide wire exchange systems.

Another object of the invention is to provide a probe attachment-detachment means comprising a coupling assembly.

Yet another object of the invention is to provide a guide wire of the above character which can be inserted, retracted or torqued in a detached mode to prevent interference with the probe handle and the ultrasound transducer.

A further object of the invention is to provide a guide wire assembly and system and apparatus utilizing the same of the above character, which permits intravascular ultrasonic tissue ablation.

Additional objects and features of the invention will appear from the following description in which the preferred embodiments are set forth in detail in conjunction with the accompanying drawings.

BRIEF DESCRIPTION OF THE DRAWINGS

In order that the invention may be more readily understood, reference is made to the accompanying figures, which illustrate diagramatically and by way of example, several embodiments thereof and in which:

FIGS. 2A and 2B show a varied diameter probe, QAD collet-horn assembly and locking nut in disassembled (2A) and assembled (2B) configurations. FIG. 2C shows an assembled configuration of a uniformly small diameter wire probe.

FIG. 3 shows a cross sectional view of the probe assembled to QAD collet (Version 1) assembly.

FIGS. 8A and 8B show the QAD collet rod and housing assemblies of the second preferred version.

FIGS. 10A and 10B show the QAD collet rod and housing assemblies of the third preferred version.

DETAILED DESCRIPTION OF THE INVENTION

Figure 1:
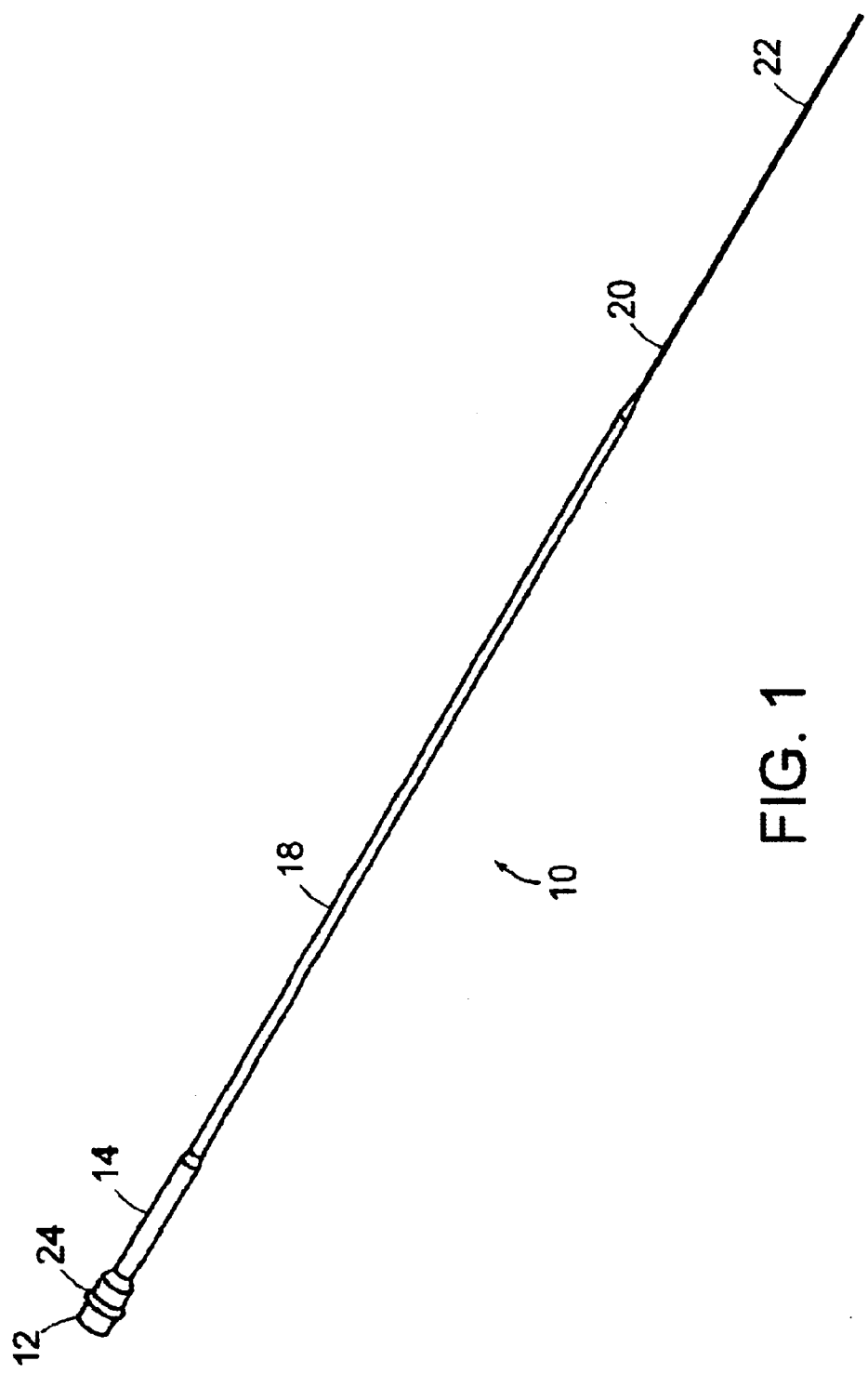
FIG. 1 is a general view of the elongated flexible wire probe catheter of the invention.

The following terms and definitions are used herein:

"Anti-node" as used herein refers to a region of minimum energy emitted by an ultrasonic probe on or proximal to a position along the probe.

"Cavitation" as used herein refers to shock waves produced by ultrasonic vibration, wherein the vibration creates a plurality of microscopic bubbles which rapidly collapse, resulting in molecular collision by water molecules which collide with force thereby producing the shock waves.

"Fenestration" as used herein refers to an aperture, window, opening, hole, or space.

"Node" as used herein refers to a region of minimum energy emitted by an ultrasonic probe at or proximal to a specific location along the longitudinal axis probe.

"Anti-node" as used herein refers to a region of maximum energy emitted by an ultrasonic probe at or proximal to a specific location along the longitudinal axis probe.

"Probe" as used herein refers to a device capable of being adapted to an ultrasonic generator means, which is capable of propagating the energy emitted by the ultrasonic generator means along its length, resolving this energy into effective cavitational energy at a specific resonance (defined by a plurality of nodes and anti-nodes at a predetermined locations (defined as "active area" of the probe) and is capable of acoustic impedance transformation of ultrasound energy to mechanical energy.

"Sheath" as used herein refers to a device for covering, encasing, or shielding in whole or in part, a probe or portion thereof connected to an ultrasonic generation means.

"Transverse" as used herein refers to vibration of a probe at right angles to the axis of a probe. A "transverse wave" as used herein is a wave propagated along an ultrasonic probe in which the direction of the disturbance at each point of the medium is perpendicular to the wave vector.

"Tuning" as used herein refers to a process of adjusting the frequency of the ultrasonic generator means to select a frequency that establishes a standing wave along the length of the probe.

The present invention provides an ultrasonic medical device operating in a transverse mode for removing a vascular occlusion by causing fragmentation of occlusion materials such as tissue. Because the device is minimally invasive, flexible and articulable, it can be inserted into narrow, tortuous blood vessels without risking damage to those vessels. Transverse vibration of the probe in such a device generates multiple nodes of cavitation energy along the longitudinal axis of the probe, which are resolved into caviational nodes emanating radially from these nodes at a specific points along the active portion of the probe. The occlusion tissue is fragmented to debris approximately of sub-micron sizes, and the transverse vibration generates a retrograde flow of debris that carries the debris away from the probe tip.

The transverse mode of vibration of the ultrasonic probe according to the invention differs from the axial (or longitudinal) mode of vibration that is conventional in the prior art. Rather than vibrating in the axial direction, the probe vibrates exclusively in a direction transverse (perpendicular) to the axial direction. As a consequence of the transverse vibration of the probe, the tissue-destroying effects of the device are not limited to those regions of a tissue coming into contact with the tip of the probe. Rather, as the active portion of the probe is positioned in proximity to an occlusion or other blockage of a blood vessel, the tissue is removed in all areas adjacent to the multiplicity of energy anti-nodes that are produced along the entire length of the probe, typically in a region having a radius of up to about 6 mm around the probe.

By eliminating the axial motion of the probe and allowing transverse vibrations only, fragmentation of large areas of tissue spanning the entire length of the active portion of the probe due to generation of multiple cavitational nodes along the probe length perpendicular to the probe axis. Since substantially larger affected areas within an occluded blood vessel can be denuded of the occluded tissue in a short time, actual treatment time using the transverse mode ultrasonic medical device according to the invention is greatly reduced as compared to methods using prior art probes that primarily utilize longitudinal vibration (along probe axis) for tissue ablation. An distinguishing feature of the present invention is the ability to utilize probes of extremely small diameter (about 0.025" and smaller) compared to prior art probes without loss of efficiency, since the tissue fragmentation process in not dependent on area of the probe tip (distal end). Highly flexible probes can therefore, be designed to mimic device shapes that enable facile insertion into highly occluded or extremely narrow interstices within blood vessels. Another advantage provided by the present invention is its ability to rapidly remove occlusion tissue from large areas within cylindrical or tubular surfaces such as arteries and arterial valves or selected areas within the tubular walls, which is not possible by previously disclosed devices that rely on the longitudinal vibrating probe tip for effecting tissue fragmentation.

The number of nodes occurring along the axial length of the probe is modulated by changing the frequency of energy supplied by the ultrasonic generator. The exact frequency, however, is not critical and a ultrasonic generator run at, for example, 20 kHz is generally sufficient to create an effective number of tissue destroying nodes along the axial length of the probe. In addition, as will be appreciated by those skilled in the art, it is possible to adjust the dimensions of the probe, including diameter, length, and distance to the ultrasonic energy generator, in order to affect the number and spacing of nodes along the probe. The present invention allows the use of ultrasonic energy to be applied to tissue selectively, because the probe conducts energy across a frequency range of from about 20 kHz through about 80 kHz. The amount of ultrasonic energy to be applied to a particular treatment site is a function of the amplitude and frequency of vibration of the probe. In general, the amplitude or throw rate of the energy is in the range of 150 microns to 250 microns, and the frequency in the range of 20,000 to 80,000 Hertz (20–80 kHz). In the currently preferred embodiment, the frequency of ultrasonic energy is from 20,000 Hertz to 35,000 Hertz (20–35 kHz). Frequencies in this range are specifically destructive of hydrated (water-laden) tissues and vascular occlusive material, while substantially ineffective toward high-collagen connective tissue, or other fibrous tissues such as, for example, vascular tissues, skin or muscle tissues.

In a preferred embodiment, the ultrasonic medical device of the present invention, comprises an ultrasonic generator that is mechanically coupled to a probe having a proximal and distal end that is capable of oscillating in a direction transverse to its longitudinal axis. Alternatively, a magnetostrictive generator may be used for generation of ultrasound energy. The preferred generator is a piezoelectric transducer that is mechanically coupled to the probe to enable transfer of ultrasonic excitation energy and cause the probe to oscillate in a transverse direction relative to its longitudinal axis. The device is designed to have a small cross-sectional profile, which also allows the probe to flex along its length, thereby allowing it to be used in a minimally invasive manner. Transverse oscillation of the probe generates a plurality of cavitation nodes along the longitudinal axis of the member, thereby efficiently destroying the occlusion. A significant feature of the invention is the retrograde movement of debris, e.g., away from the tip of the probe i.e. backwards up along the shaft of the probe that results from the transversely generated energy. The amount of cavitation energy to be applied to a particular site requiring treatment is a function of the amplitude and frequency of vibration of the probe, as well as the longitudinal length of the probe tip, the proximity of the tip to a tissue, and the degree to which the probe tip is exposed to the tissues.

A distinguishing feature of the present invention is the ability to utilize probes of extremely small diameter (narrow diameter probes) compared previously disclosed devices (large diameter probes) without loss of efficiency or efficacy, since the tissue fragmentation process in not dependent on area of the probe tip (distal end). Highly flexible probes can therefore be obtained to mimic device shapes that enable facile insertion into highly occluded or extremely narrow interstices without resulting in breakage of the probe or puncture or damage of the tissue or body cavity while ensuring optimal results.

A second distinguishing feature of the small diameter probes of the invention is that the probe diameter is approximately the same over their entire length, that is,—the active tip segment (distal end) and the rear segment (proximal end) of the probes are approximately similar in diameter. In a preferred embodiment the probe diameters at the proximal and distal ends respectively are about 0.025 inch. An advantage of the shape configuration of the probes of the invention is that they are adaptable to currently used standard vascular introducers. Since the rear segment (proximal end) of the probes have no non-cylindrical shape or "bulk", catheters and guides can be introduced over the ends of the elongated wire probes of the invention, thereby—allowing their use in standard-configuration endovascular procedures.

The ultrasonic device of the invention comprises a longitudinal resonator such as for example, a Mason (Langevin) horn that is in intimate contact with an elongated catheter wire probe through a coupling assembly. The horn assembly is in turn, connected to an ultrasound energy source. Upon device activation, ultrasonic energy from the source is transmitted to the horn assembly wherein it is amplified by the horn and in turn, transmitted to the probe thorough the coupling assembly. Transverse vibrational modes along the longitudinal axis of the probe that lie within the horn resonance are excited.

The coupling between the elongated probe and the horn is adjusted so as to present a relatively large impedance mismatch, and be located at a node of the horn. Longitudinal waves impinging on the coupling interface are either reflected back into the horn or transmitted out to the probe in proportion to the degree of impedance mismatch at the said coupling interface. In a preferred embodiment, the coupling interface is configured in a manner so as to reflect most of the energy back into the horn. The horn therefore, essentially acts as an energy storage device or "reservoir", thereby allowing a substantial increase in drive amplitude.

Since the energy coupled into the elongated probe is a small portion of the energy reflected back to the horn, changes in the transverse oscillation on the probe due to bending or damping have minimal effect on the longitudinal resonance of the horn. By decoupling the transverse probe oscillation from the longitudinal horn resonance, the electrical source of the vibrations (piezoelectric or magnetostrictive) to compensate only for shifts in the resonant frequency of the horn (due to temperature, manufacturing variations, etc.). The drive mechanism is therefore, completely independent of vibrational motions on the probe.

The transverse vibrating elongated probe of the invention does not require its terminal end be permanently affixed in intimate contact to the horn assembly, since a "hammering" action associated with longitudinal vibration is absent. The elongated probe of the invention can therefore be coupled, and not welded, to the horn via a coupling assembly that grips the probe along the cylindrical surface near its terminal end in a non-permanent way. The coupling assembly of the invention therefore, allows for quick attachment and detachment of the probe from the horn assembly and source components, thereby enabling manipulation of the elongated flexible probe into anatomically curved blood vessels without hindrance by the bulky horn and energy source components. The probe of the invention can therefore be inserted into a venal cavity, positioned near the occlusion site prior to coupling it to the horn source assembly. The device is then activated to effect tissue ablation and removal, after which the probe is decoupled from the horn and source component for its easy removal from the cavity.

In a preferred embodiment a longitudinal horn is coupled to an elongated wire catheter through a coupling assembly that is rapidly attachable and detachable. In a most preferred embodiment, the coupling assembly comprises a quick attachment-detachment (QAD) collet. The attachment of the coupling assembly to the elongated probe is located at a node and the dimensions are scaled (the collet head has a relatively larger diameter at the attachment point than the diameter of the probe) to produce an optimal impedance mismatch. In another embodiment of the invention, the elongated probe is permanently attached to the coupling assembly by a welded joint.

The QAD collet of the invention is housed within an externally mounted compressive clamp that is capable of exerting a compressive force on the collet after insertion of the ultrasonic probe into said collet, thereby causing a non-removable attachment of the probe to the coupling assembly. The collet therefore, applies a restraining inwardly compressive force on the probe in a manner so as to not torque or twist the probe material. As a result, the probe can be subject to a multiple attachment and detachment procedures, without causing probe destruction, thereby enabling its extended reuse in surgical procedures.

The collet of the invention comprises is at least one slit in its terminal compressible segment; alternatively it comprises of a plurality of slits. In a preferred embodiment, the collet, compressive clamp and housing assembly are all attached to the device handle by a mechanical assembly means, such as for example, a screw thread comprising a locking nut, bayonet mount, keyless chuck and cam fittings. Alternatively, the rear segment of the mechanical assembly means is a hollow cylindrical segment comprising a screw thread that allows insertion and attachment of the ultrasonic device handle containing a drive assembly containing a complementary thread arrangement to be inserted into and non-removably attached to said cylindrical segment by applying a torque. In another preferred embodiment, ultrasonic probe is mounted to the attachment means such that the collet holds the probe at a point greater than about 1 mm and less than about 30 from the probe terminal end, or is adjustable to any point in between, to optimize probe vibration based on the frequency of the ultrasound transducer in the device handle. In another preferred embodiment, the probe attachment means comprising the external compressive clamp, collet and collet housing are all attached to the operating handle of the ultrasonic device.

In another preferred embodiment the collet is retained within the confines of an outer shell that is attached to the collet housing segment of the probe attachment means that to precludes its disassembly, thereby preventing either loss or disengagement of the collet. The outer shell compresses the collet to engage contact with the probe upon its tightening to the collet housing assembly by application of torque, causing the probe to be attached to the collet in a non-removable manner. An inner bias is maintained within the rear portion of the attachment means such that a portion of the probe protruding from the proximal end of the collet maintains contact with the surface of the collet housing within the coupling assembly.

The terminal ends of the collet are tapered so as to allow the collet to maintain a true axial orientation within the coupling assembly, thereby enabling multiple insertions and retractions of the probe into and from the collet prior to and after device use, without causing the probe to kink. Additionally, the shape of the proximal end of the segment (rear segment with respect to the entering probe), so as to maximize contact area between the collet and the distal end of the transducer-sound conductor assembly (the "drive assembly"). The collet proximal end is shaped in any suitable form providing maximal contact area, including conical, frusto-conical, triangular, square, oblong, and ovoid, upon probe attachment to the collet within the housing assembly, which in turn maintains intimate contact with the drive assembly. The four component assembly that include probe, outer ring, collet and rear drive assembly, form a single assembled component in the device operational state, in terms of their combined ability to transmit sound energy from the transducer in the drive assembly to the probe without energy loss thermally or mechanically. The collets of the invention can be designed to accommodate a series of probe diameters, or for a specific probe diameter by varying the inner diameter of the cylindrical slot. The outer diameters of the collets, however remain unchanged, thereby allowing attachment of probes of differing diameters into a universal coupling and drive assembly.

The elongated probe of the invention is either a single diameter wire with a uniform cross section offering flexural stiffness along its entire length, or is tapered or stepped along its length to control the amplitude of the transverse wave along its entire longitudinal axis. Alternatively, the probe can be cross-sectionally non-cylindrical that is capable of providing both flexural stiffness and support energy conversion along its entire length. The length or the elongated probe of the invention is chosen so as to be resonant in either in an exclusively transverse mode, or be resonant in combination of transverse and longitudinal modes to provide a wider operating range. In a preferred embodiment, the elongated probe of the invention is chosen to be from about 30 cm to about 300 cm in length. In a most preferred embodiment, the elongated probe of the invention has a length of about 70 cm to about 210 cm in length. Suitable probe materials include metallic materials and metallic alloys suited for ultrasound energy transmission. In a preferred embodiment the metallic material comprising the elongated probe is titanium.

In another preferred embodiment, the elongated probe of the invention is circumferentially enclosed in a sheath that provides a conduit for irrigation fluids, aspiration of fragmented tissue, or for delivery of therapeutic drugs to the occlusion site. The said sheath can extend either partially or over the entirety of the probe, and can additionally comprise of fenestrations for directing ultrasonic energy from the probe at specific locations within venal cavities for selective ablation of tissue. An ultrasonic tissue ablation device comprising a sheath for removal of occlusions in blood vessels has been disclosed in applicants' co-pending application Ser. No. 09/776,015, the entireity of which is incorporated herein as reference.

In one embodiment, the elongated catheter probe is comprised of a proximal end and a distal end with respect to the horn assembly, and is in the form of a long small diameter wire incorporating a series of telescoping segments along its longitudinal axis, such that the largest diameter segment is proximal to the horn assembly, and either continually or segmental, sequentially decreasing diameters from the proximal to the distal end. With reference to the probe, coupling and horn assemblies as shown in the figures describing the present invention, the proximal end for each component refers to the end farthest from the probe tip, while distal end refers to the end closest to the probe tip. In another embodiment, the elongated probe is comprised of a non-segmented, uniformly narrow diameter wire, such as for example a guide wire, such as those used in insertion of catheters.

Referring now to FIG. 1, a preferred embodiment of the elongated ultrasonic probe 10 of the invention comprising a proximal end 12 and a distal end 22, is shown. Probe 10 is coupled to a transducer and sound conductor assembly (not shown) constructed in accordance with the present invention that function as generation and transmission sources respectively, of ultrasound energy for activation of said probe. The generation source may or may not be a physical part of the device itself. The probe 10 transmits ultrasonic energy received from the sound conductor along its length, and is capable of engaging the sound conductor component at its proximal end 12 via a coupling assembly with sufficient restraint to form an acoustical mass that can propagate the ultrasonic energy provided by the source. The probe diameter decreases at defined segment intervals 14, 18, and 20. Segment 22 because of its small diameter, is capable of flexing more than segments 14 and 18, thereby enabling probe 10 to generate more cavitation energy along segment 20 distal end 22. Energy from the generator is transmitted along the length of the probe, causing the probe to vibrate in a direction that is transverse to its longitudinal axis. Probe interval 14 has a head segment 24 for engaging the coupling assembly for attachment to the sound conductor-transducer assembly. In a preferred embodiment, the sound conductor component of the invention for providing, amplifying and transferring ultrasonic energy to elongated probe 10 is a Mason (Langevin) horn that is detachably connected to said probe through a coupling assembly.

Referring now to FIGS. 2A–B, the unassembled and assembled views of individual components comprising the varied diameter probe and sound conductor elements, and the coupling assembly are illustrated. FIG. 2A shows the individual components comprising elongated probe 10, horn assembly 34 comprising a proximal end 38 and a comprising a cylindrical slot 36 at the distal end, which includes the horn and coupling assembly components, elongated probe 10 and locking nut 30. The coupling assembly components comprising threading arrangements 40 and 42, cylindrical slot 36, and locking nut 30. Attachment of proximal end 12 of probe 10 is accomplished by insertion of probe head 24 into the cylindrical slot at distal end 36 of the horn assembly, followed by "threading" the probe through locking nut 30 to enable threads on the inner surface of locking nut 30 (not shown) to engage complementary threads 40, thereby providing intimate contact between probe distal end 12 and the proximal end 36 of the horn assembly. The probe attachment is rendered to be mechanically rigid by tightening locking nut 30. FIG. 2B shows the enlongated varied diameter probe attached to the horn assembly and held rigidly by the coupling assembly and maintaining intimate contact between the "coupled" components. FIG. 2C shows a similar assembly comprising a uniform narrow diameter wire probe of the invention.

Figure 4B:
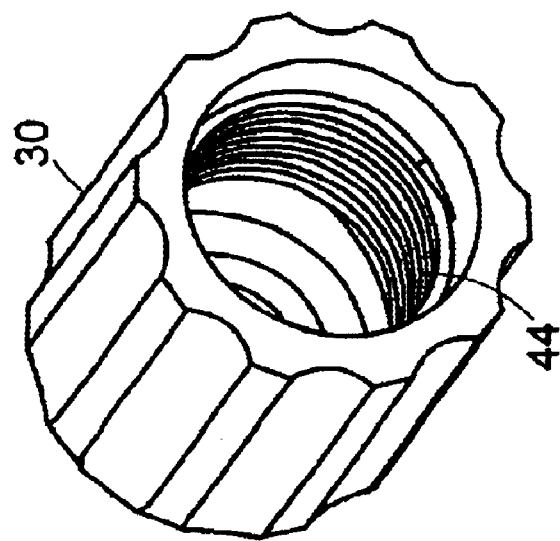
FIGS. 4A and 4B show the locking nut viewed from the opposite cylindrical ends.
Figure 4A:
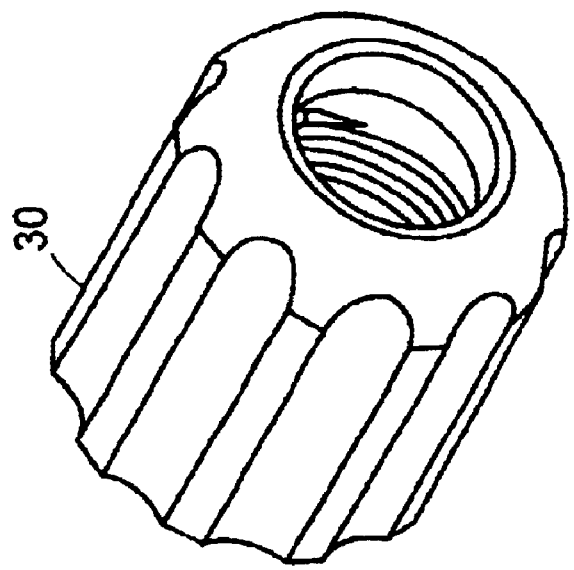
Figure 5:
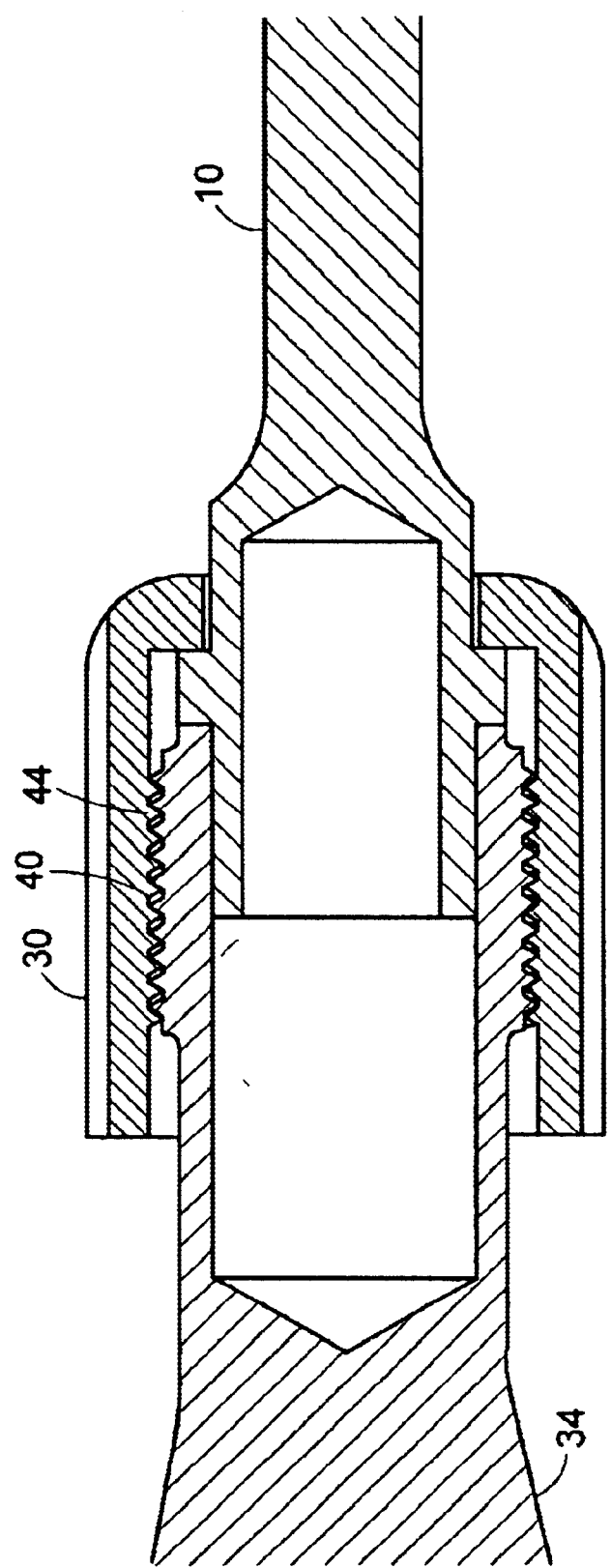
FIG. 5 shows a cross sectional view of the locking nut coupling the probe to the QAD collet-horn assembly.

FIG. 3 shows a cross-sectional view of the probe-horn assembly shown in a "coupled" mode. The attachment means comprising the coupling assembly of the invention utilized to "couple" the elongated probe to the horn assembly is chosen from conventional means of connecting physically separated components in a manner so as to provide a rigid joining of said components while maintaining intimate material surface contact between the components in the "coupled" state. Suitable attachment means of the present invention include a locking nut comprising a screw thread, and a bayonet or ring clamp mechanism to effect coupling between the elongated probe and the horn assembly. FIGS. 4A and 4B show opposite-end views of a preferred embodiment of the locking means, comprising a locking nut 30 consisting a screw thread arrangement 44 that is capable of engaging a complementary thread arrangement located along the outer diameter of the distal end of the horn assembly. When engaged with the horn assembly 34 with the elongated probe 10 positioned proximally to provide "coupling", locking nut 30 provides a rigid interface between the probe and horn components and ensures intimate contact between the terminal end surfaces of the said components, which is important for efficient transmission of ultrasound energy to the probe. FIG. 5 shows a cross-sectional view of the horn assembly 34 and elongated probe 10 "coupled" by the locking nut 30 of the invention by engaging screw thread 44 with complementary threads 40 in the horn assembly.

Figure 6:
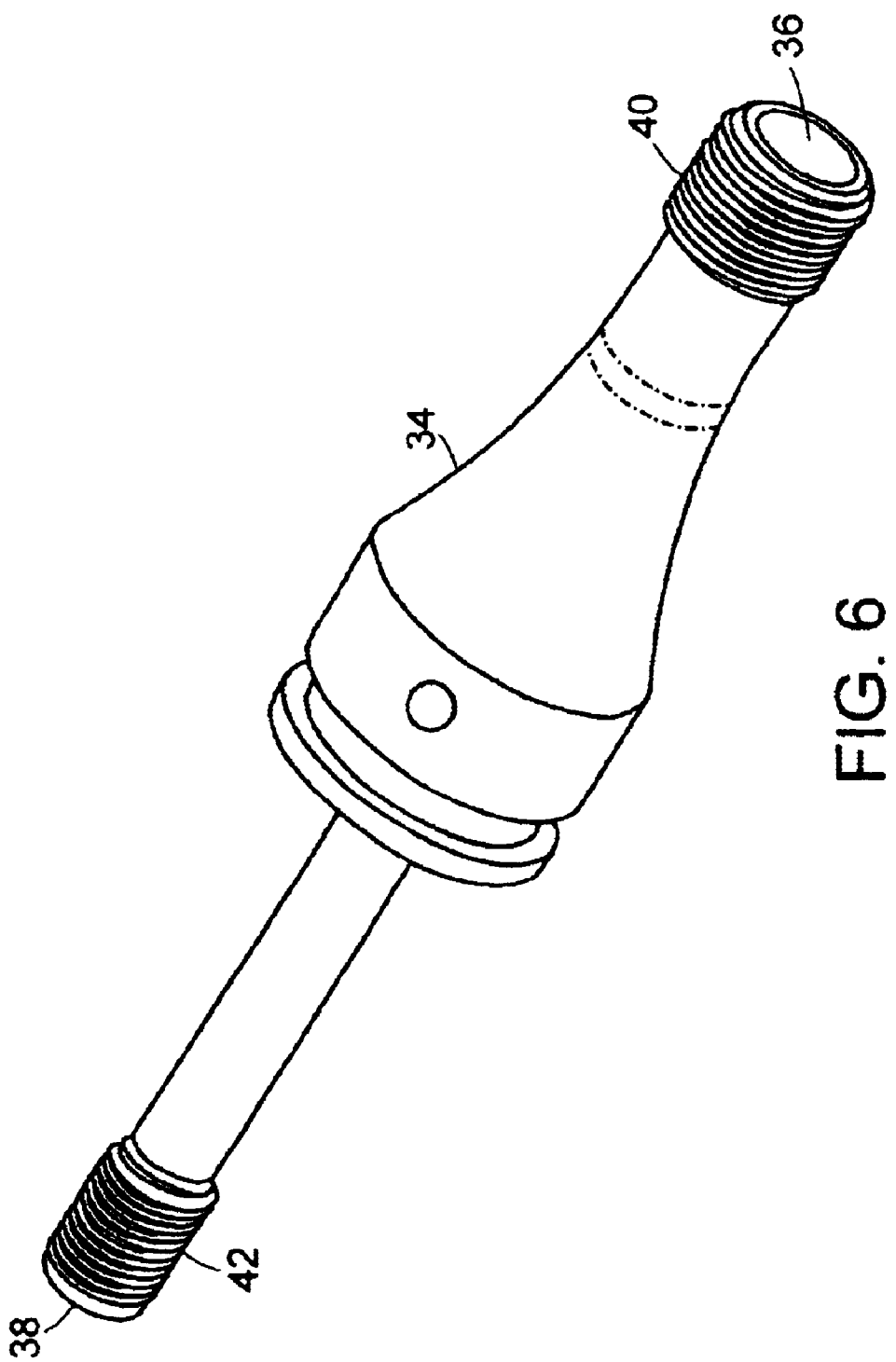
FIG. 6 shows the threaded horn component of the QAD collet-horn assembly.

Now referring to FIG. 6, the horn assembly 34 comprises of a distal end 38 that is capable of being coupled to the enlongated probe of the invention, and a proximal end 38 that is coupled to a transducer (not shown) functioning as an ultrasound energy source by screw threads 40 and 42 located terminally at either end. As mentioned previously, horn assembly 34 comprising the sound conductor or "horn" functions as an energy reservoir that allows only a small fraction of the energy transmitted by the source to the probe, thereby minimizing energy loss due to probe bending or damping that can occur when it is inserted into blood vessels.

Figure 7:
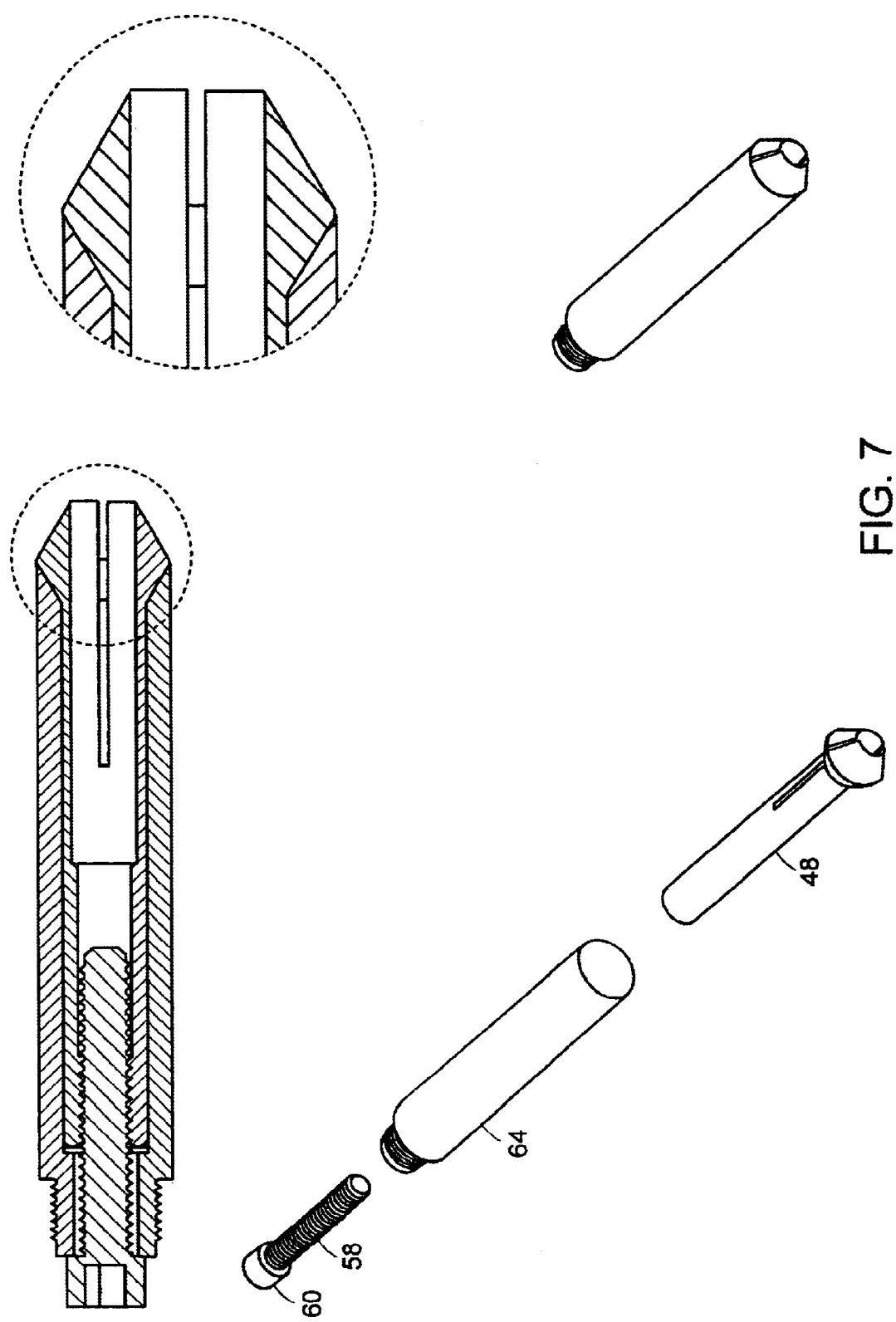
FIG. 7 shows scaled and cross-sectional views of a second preferred version of the QAD collet assembly.

FIG. 7 shows disassembled and assembled views of another preferred embodiment of the probe attachment means of the invention, including cross-sectional views in the assembled state, that includes a coupling assembly comprising a "quick attachment/detachment" (QAD) collet rod 48 and housing assembly 54 that enables efficient coupling of the elongated catheter probe to the horn assembly (not shown). As seen in the figure, collet rod 48 is configured to slideably receive and retain the proximal end of the ultrasonic probe of the invention within the interior volume of collet housing 64, and restrained in a rigid, non-removable manner by socket screw 58, which comprises a cylindrical head 60 with a uniformly flat end to facilitate its intimate contact with other device components, including the terminal end of the horn assembly. FIG. 7 also shows regular and expanded cross-sectional views of QAD collet rod 48 inserted into collet housing 64 that is non-removably retained within said housing by socket screw 58. As seen in segment "C" of the cross-sectional view, the inner surface of collet housing tapers circumferentially outwardly at the distal end so as to enable partial insertion of the cylindrically slotted head of the QAD collet rod. The inner diameter of the of the circumferentially tapered section of the housing is chosen to be slightly larger then the insertable segment QAD collet rod head so as to create a "clearance" that facilitates easy insertion and retraction of the said collet rod (shown in the detail cross-sectional view in FIG. 7).

As shown in FIG. 8A, QAD collet rod 48 is comprised of a hollow cylindrical segment 49 with a proximal end 50 and a head segment 51 at distal end 52 (the end farthest from the collet housing and horn assembly) with a diameter larger than that of cylindrical segment. The head segment at distal end 52 comprises a compressible slit 54 that is capable of accommodating the proximal end of the elongated probe. The proximal end 50 of the QAD collet rod comprises a hollow cylindrical opening containing a screw thread inscribed along the inner surface of said opening that is capable of receiving a retaining a socket screw 58 (shown in FIG. 7) inserted from the proximal end of the QAD collet housing, so as to render collet rod 48 with attached probe to be rigidly and non-removably restrained within said collet housing. As shown in FIG. 8B, collet housing 64 comprises a hollow cylinder with a distal end 68 capable receiving the entire cylindrical segment 49 of the probe QAD collet rod (FIG. 8A) and part of the cylindrically slotted head segment 51 when the collet rod is inserted at its proximal end 50 into collet housing 64, and a distal end 72 comprising a screw-thread 74 along the outer surface. The proximal end 72 of collet housing further comprises a screw thread 74 on its outer surface capable of engaging the terminal end of a horn assembly in a manner so as to provide intimate contact between the horn and the flat head of socket screw 58 restraining QAD collet rod 48 attached to the elongated probe, thereby enabling transmission of ultrasound energy from the horn to the elongated probe.

The socket screw 58 of the invention is capable of being "tightened" by applying a torque by conventional methods causing it to simultaneously engage the thread assemblies if of collet rod housing 64 and the QAD collet rod 48 respectively, after insertion of the collet rod into said housing. Such a tightening action which is performed after attachment of the elongated probe to collet rod 48 by insertion of the probe into slotted head 54 at the distal end 52 of the collet rod causes retraction of the said slotted head into the collet housing. This in turn, results in elimination of the "clearance" between the collet rod and the collet housing, causing a contraction in the diameter of the slot in the head of collet rod and in turn, resulting in 1) its intimate contact with the surface of the proximal end of the inserted elongated probe, and 2) restraining the probe in a non-detachable manner to the collet rod—housing coupling assembly. The rigid and non-removable mode of probe attachment to the said coupling assembly enables transmission of ultrasound energy from a horn assembly attached to the collet rod-housing coupling assembly to the elongated probe so as to cause it to vibrate in a transverse mode, and hence provide cavitation energy for tissue destruction. Conversely, the probe is detached (or "de-coupled") from the collet rod-housing coupling assembly by loosening the socket screw 58 by application of a torque in a direction opposite to that used for the probe attachment process.

Figure 9:
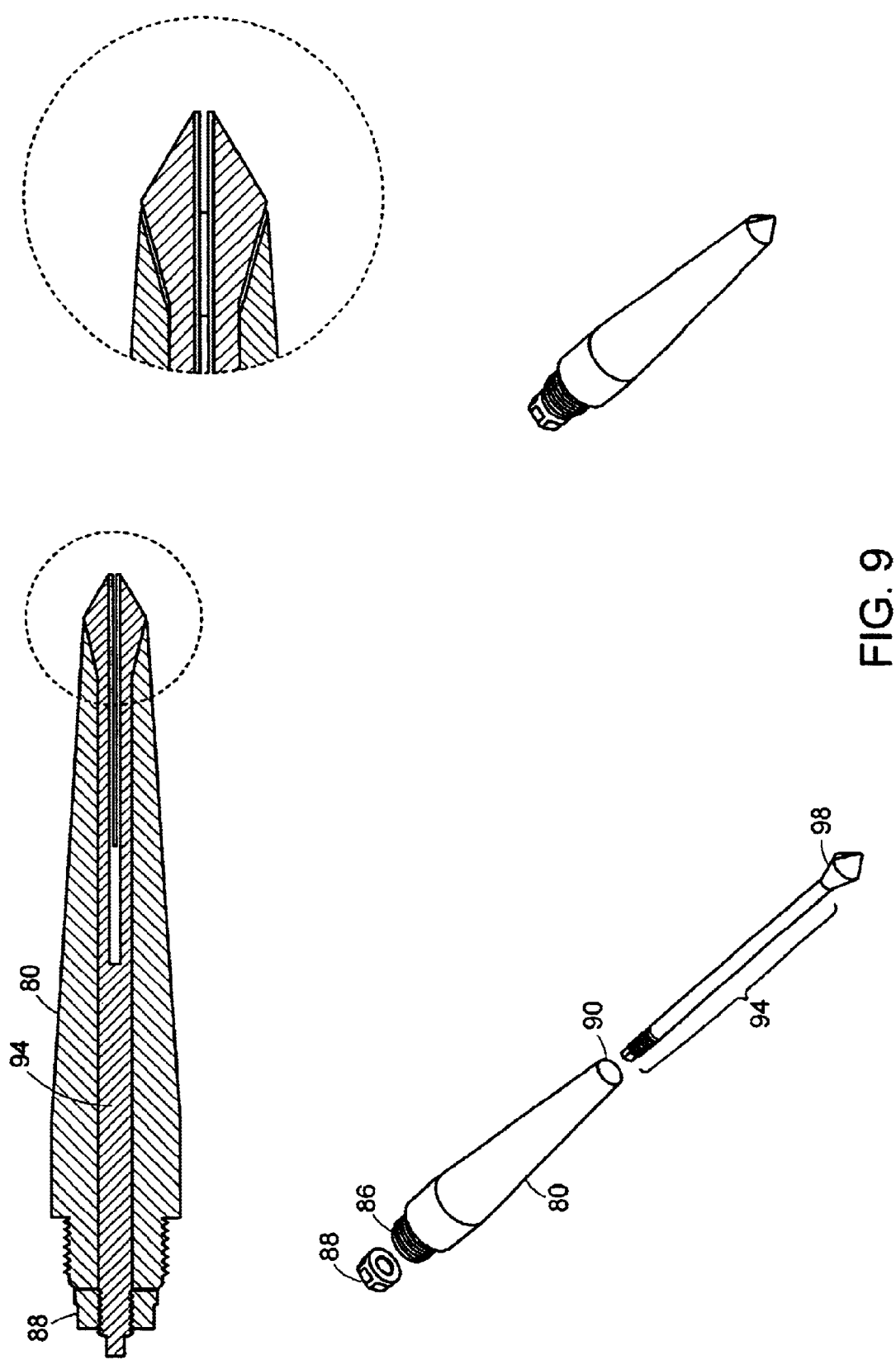
FIG. 9 shows scaled and cross-sectional views of a third preferred version of the QAD collet assembly.

FIG. 9 shows disassembled and assembled views of another preferred embodiment of the probe attachment means of the invention, including cross-sectional views in the assembled state, consisting a QAD collet rod-housing assembly that comprises a outwardly cylindrically tapered collet housing component 80 with a proximal end 86 and a distal end 90, further comprising a centrally located cylindrical bore with open ends extending through its longitudinal axis that is capable of slideably receiving and retaining a collet rod. As seen in segment "C" of the cross-sectional view in FIG. 9, the inner surface of collet housing tapers circumferentially outwardly at the distal end so as to enable partial insertion of the cylindrically slotted head of the QAD collet rod. The inner diameter of the of the circumferentially tapered section of the housing is chosen to be slightly larger then the insertable segment QAD collet rod head so as to create a "clearance" that facilitates easy insertion and retraction of the said collet rod (shown in the detail cross-sectional view). The cross-sectional view of the FIG. 9 shows the QAD collet rod restrained within the collet rod housing by a locking nut 88. FIGS. 10A and 10B show the collet rod and collet housing respectively, of the embodiment. As seen in FIG. 10A, QAD collet rod comprises a solid cylindrical body 94 with a head segment 98 attached at proximal end 92. A longitudinal slit 99 extends from head segment 98 partially into the cylindrical body 94. The distal end 96 of cylindrical body 94 comprises a thread assembly 100. As seen in FIG. 10B, collet housing 80 comprises a cylindrical rod with a continuously decreasing external diameter from proximal end 86 to distal end 90, further comprising a centrally located cylindrical inner bore extending along its entire length providing openings at both ends. The diameter of the bore increases proximally to the distal end so as to circumferentially taper outwardly in a manner permitting partial insertion of head segment 98 of the collet rod The cylindrical bore of the collet housing 80 is capable of slideably receiving a collet rod 94 such that thread assembly 100 of the said collet rod extends beyond proximal end 86 of the end proximal end 92 to permit a rigid and non-removable attachment of the collet rod by engaging thread assembly 100 with locking nut 88 (shown in FIG. 9). The locking nut performs a similar function and in a manner that is substantially similar to that of the restraining screw described in a previous embodiment (FIG. 7) in enabling the elongated probe to be non-removably attached to and detached from the QCD collet rod for operation of the device as described previously. Upon rigid non-removable attachment of the elongated probe to the coupling assembly, the threading 88 of the collet housing is engaged to complementary threading of the horn assembly (not shown) of the assembly so as to render intimate contact of the sound conductor (horn) in said horn assembly with the proximal end 92 of the collet rod to enable transmission of ultrasound energy from the horn to the elongated probe attached at proximal end 96 of the collet rod.

Figure 11:
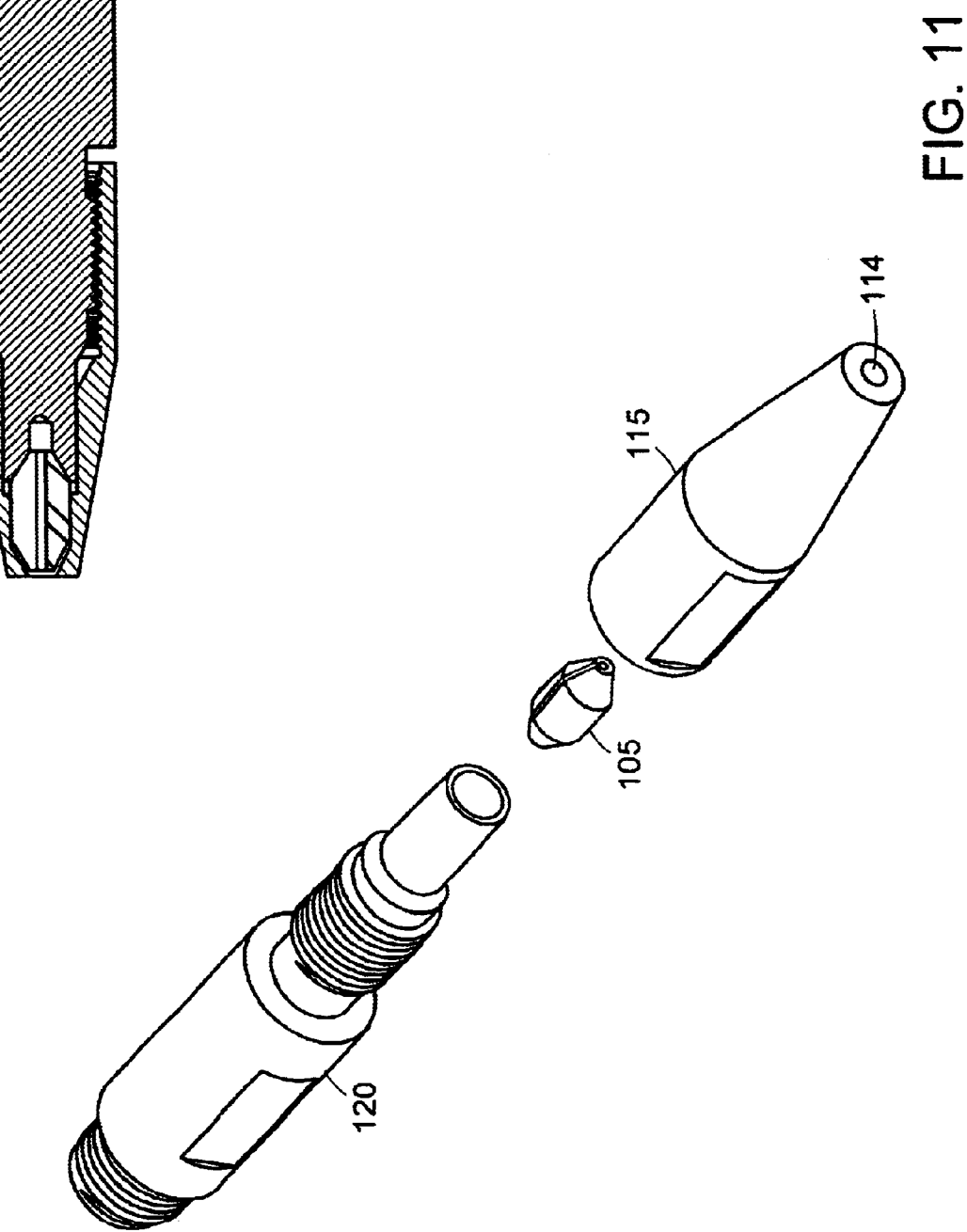
FIG. 11 shows scaled and cross-sectional views of a fourth preferred version of the QAD collet assembly.
Figure 12A:
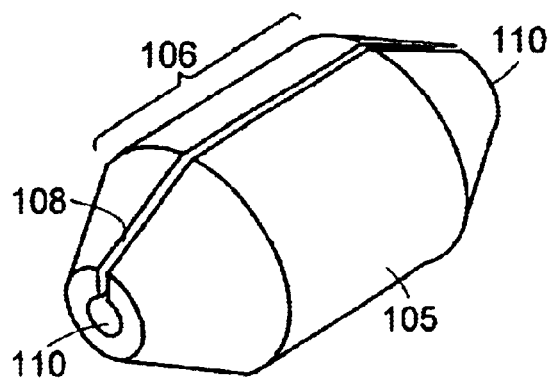
FIGS. 12A, 12B and 12C show the collet, QAD base component and compression housing of the fourth preferred version.
Figure 12B:
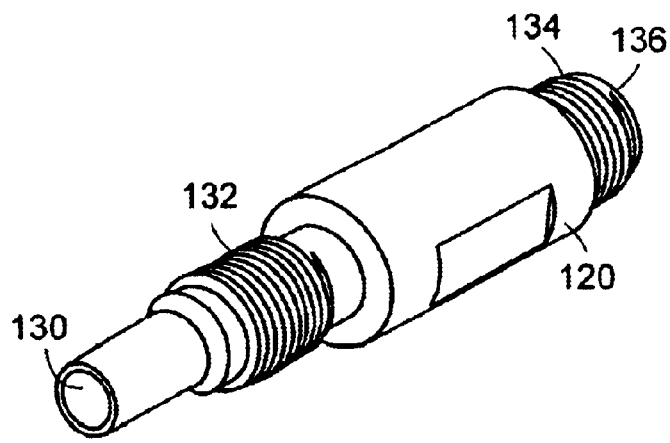
Figure 12C:
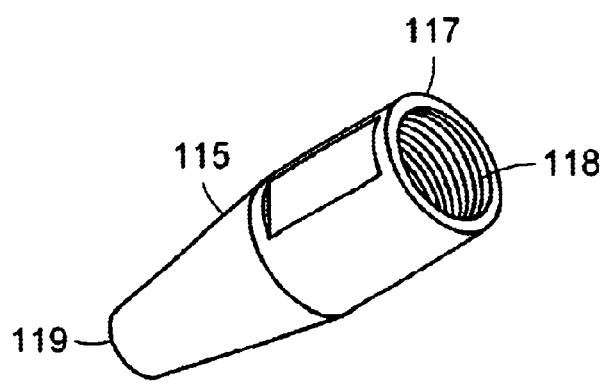

FIG. 11 shows another preferred embodiment of probe coupling assembly of the invention, including a cross-sectional view, comprising a QAD collet 105 that is insertable into a "compression" collet housing component 115 comprising a circular bore 114 that is detachably connected to a QAD base component 120. As seen in FIG. 12A, QAD collet 105 comprises a cylindrical segment 106 with a cylindrical slot 108 extending through its longitudinal axis that is capable of slideably receiving the proximal end of the elongated probe, and symmetrically tapered at proximal and distal ends 110. As seen in FIG. 12B, QAD base component 120 comprises a conical slot 130 at the cylindrical distal end capable of accommodating the one of the symmetrically tapered ends 110 of the collet. QAD base component 120 further comprises a thread assembly 132 located along its outer circumference proximal to its distal end, that is capable of engaging complementary threads in the QAD compression housing component 115. The proximal end 136 of the base component contains a thread assembly 134 along the outer circumference that is capable of engaging and attaching to the horn assembly (not shown) of the invention. As seen in FIG. 12C, QAD compression housing component 115 comprises a hollow cylindrical segment with a proximal end 117 and a circular bore 114 (shown in FIG. 11) tapered distal end 119 capable of slideably receiving the proximal end of the elongated probe. The inner diameter at the proximal end of the QCD compression housing component 115 is chosen so as to accommodate the symmetrically tapered terminal end 110 of collet 105 that is distal to the base component, and further comprises a thread assembly 118 that enables compression housing component to engage with complementary threading 132 on the distal end of QAD base component 120. The proximal end of the elongated probe of the invention is inserted through the circular bore 114 at proximal end of compression housing component 115 and the inserted symmetrically tapered end 110 of collet 105 in a manner so as to occupy the entire length of cylindrical slot 108 in collet 105. The other symmetric end 110 distal to the compression housing 115 is then placed inside conical pocket 130 of base component 120, following which threads 118 of the compression housing is engaged with the complementary threads 132 in QAD base component 120 by applying a torque so as to render the collet 105 to be non-removably retained inside the coupled base-compression housing assembly, thereby restraining the inserted elongated probe rigidly and non-removably within the coupling assembly. Additionally, the mode of restraint provided by the coupling assembly of the embodiment enables the probe to maintain intimate contact with said assembly and in turn the horn assembly (not shown) of the invention attached to the coupling assembly by engaging thread 134 in QAD base component 120 with complementary threading in the horn assembly. Ultrasound energy transmitted from the horn is therefore communicated to the probe via the coupling assembly. The elongated probe is detached by disassembling the coupling assembly, thereby allowing the probe to be withdrawn from collet 105 and compression housing component 115.

The device of the invention upon being activated causes the ultrasound generator component to transmit ultrasonic energy to the horn component. The transmitted energy is amplified by the horn component, which in turn, due to it's intimate and proximal contact with the elongated probe, transmits the amplified energy to the said probe. Transverse vibration modes on the elongated probe that fall within the horn resonance are therefore, excited. The "coupling" between the elongated probe and the horn is configured so to as to present a relatively large impedance mismatch. The coupling is located at a node of the horn. Longitudinal waves impinging on the coupling will be either reflected back inside the horn, or transmitted outward to the elongated probe proportionally to the degree of the impedance mismatch at the coupling interface. In a preferred embodiment, the coupling is arranged in a manner so as to cause reflection of a substantial portion of ultrasound energy back into the horn. Under these conditions, the horn essentially functions as an energy storage device or reservoir, thereby allowing for a substantial increase in drive amplitude.

The ultrasonic device of the present invention provides several advantages for tissue ablation within narrow arteries over convention devices. The transverse energy is transmitted extremely efficiently, and therefore the required force to cause cavitation is low. The transverse probe vibration provides sufficient cavitation energy at a substantially low power (~1 watt). Because transverse cavitation occurs over a significantly greater i.e. along the entire probe longitudinal axis that comes in contact with the tissue, the rates of endovascular materials that can be removed are both significantly greater and faster than conventional devices. The transverse vibrational mode of the elongated probe of the invention and its attachable/detachable coupling mode to the horn assembly allows for the bending of the probe without causing probe heating as heat in the probe.

Another advantage offered by the device of the invention is that the mechanism for probe attachment and detachment by means of a lateral wall compression and decompression provided by the coupling assembly. The probe can therefore, be rapidly attached to and detached from the coupling assembly without necessitating its "screwing" or "torquing" that are utilized conventional modes of attachment of ultrasonic probes to the probe handle. This feature facilitates ease of manipulation of the probe within narrow and torturous venal cavities, and its positioning at the occlusion site in a manner substantially similar to narrow lumen catheters prior to and after device use.

What is claimed is:

1. A device for removing occlusions in blood vessels comprising:

a) an ultrasonic probe having a proximal end and a distal end;
b) a probe attachment means including a coupling assembly; and
c) a sound conductor with a proximal end and a distal end, said distal end being connected to the coupling assembly and said proximal end being connected to a transducer capable of providing ultrasound energy,
wherein said ultrasonic probe is releasably mounted at said proximal end to said probe attachment means, enabling said sound conductor to transmit ultrasound energy from said transducer to said ultrasonic probe, causing said ultrasonic probe to vibrate in a direction substantially transverse to a longitudinal axis of said ultrasonic probe producing a plurality of transverse vibration anti-nodes along at least a portion of the longitudinal axis of the ultrasonic probe.

2. The device of claim 1 wherein the ultrasonic probe is a flexible elongated wire.

3. The device of claim 1 wherein the ultrasonic probe is a catheter guide wire.

4. The device of claim 1 wherein the ultrasonic probe supports a standing transverse sound wave to generate an ultrasonic cavitation energy in an at least one location along the longitudinal axis of the ultrasonic probe.

5. The device of claim 4 wherein said ultrasonic cavitation energy is preferentially enhanced at the distal end of said ultrasonic probe.

6. The device of claim 1 wherein a flexural stiffness of the ultrasonic probe varies along the longitudinal axis of the ultrasonic probe.

7. The device of claim 1 wherein the ultrasonic probe is a vascular guidewire.

8. The device of claim 1 wherein a dimension of the ultrasonic probe remains unchanged along the longitudinal axis of the ultrasonic probe.

9. The device of claim 1 wherein a length of the ultrasonic probe is between about 30 centimeters and about 300 centimeters.

10. The device of claim 1 wherein a length of the ultrasonic probe is between about 50 centimeters and about 90 centimeters.

11. The device of claim 1 further comprising a sheath assembly that includes at least one sheath extending over a portion of the ultrasonic probe.

12. The device of claim 11 wherein the sheath assembly substantially prevents transmission of a cavitational energy generated by said ultrasonic probe to a surrounding environment.

13. The device of claim 11 wherein the sheath assembly further comprises at least one fenestration.

14. The device of claim 13 wherein the fenestration is capable of transmitting a cavitation energy therethrough to a surrounding environment.

15. The device of claim 11 wherein the sheath assembly further comprises at least one reflective element.

16. The device of claim 11 wherein said sheath assembly further comprises at least one irrigation channel.

17. The device of claim 11 wherein said sheath assembly further comprises at least one aspiration channel.

18. The device of claim 11 wherein said sheath assembly further comprises at least one channel for delivering a therapeutic agent therethrough.

19. The device of claim 11 wherein said sheath assembly further comprises an imaging device.

20. The device of claim 11 wherein the sheath assembly is adapted for use with an imaging system.

21. The device of claim 11 wherein the sheath assembly is a vascular catheter comprising at least one lumen.

22. The device of claim 1 wherein the probe attachment means comprises a coupling assembly capable of connecting the longitudinal axis of the ultrasonic probe to the sound conductor and the transducer capable of vibrating at an ultrasonic frequency.

23. The device of claim 1 further comprising a handle comprising the sound conductor and the transducer.

24. The device of claim 1 wherein the sound conductor comprises a horn assembly capable of providing an impedance mismatch between said sound conductor and the ultrasonic probe.

25. The device of claim 1 wherein the coupling assembly comprises a releasable compressive clamp mounted externally to a collet residing in a housing assembly at a distal end of said coupling assembly, said collet capable of releasably engaging the ultrasonic probe.

26. The coupling assembly of claim 25 wherein the releasable compressive clamp is capable of exerting a compressive force on the collet causing said collet to engage the ultrasonic probe.

27. The device of claim 25 further comprising a plurality of attachment and detachment means of the ultrasonic probe.

28. The device of claim 1 further comprising a handle containing the probe attachment means comprising an external compressive clamp, a collet and a collet housing.

29. The device of claim 1 wherein the sound conductor connected to the coupling assembly is capable of controlling an ultrasound energy transferred to the ultrasonic probe.

30. A method of removing a vascular occlusion in a blood vessel comprising the following steps:
  a) detaching an ultrasonic probe from a probe attachment means;
  b) inserting the ultrasonic probe into a site of the occlusion;
  c) positioning the ultrasonic probe at said site of said occlusion by a manipulation within the blood vessel having the occlusion;
  d) mounting the ultrasonic probe to a coupling assembly;
  e) activating a transducer to vibrate the ultrasonic probe in a direction substantially transverse to a longitudinal axis of the ultrasonic probe producing a plurality of transverse vibration anti-nodes along at least a portion of the longitudinal axis of the ultrasonic probe; and
  f) detaching the ultrasonic probe from the coupling assembly upon completion of a surgical procedure and withdrawing the ultrasonic probe from the blood vessel.

31. The method of claim 30 providing the ultrasonic probe that is a flexible elongated wire.

32. The method of claim 30 providing the ultrasonic probe that is a catheter guidewire.

33. The method of claim 30 providing the ultrasonic probe that comprises a sheath assembly comprising at least one sheath.

34. The method of claim 33 providing the sheath that is capable of partially shielding a tissue at a site of a surgical procedure from said ultrasonic probe.

35. The method of claim 33 providing the sheath assembly that comprises an aspiration conduit, whereby fragments of an occlusion material are removed through said aspiration conduit.

36. The method of claim 33 wherein the sheath assembly further comprises an irrigation conduit to supply an irrigating fluid to the site of the occlusion.

37. The method of claim 33 wherein the sheath assembly comprises a conduit for delivering a therapeutic agent therethrough.

38. The method of claim 33 providing the sheath assembly that comprises an imaging system to enable positioning of said ultrasonic probe proximal to said occlusion.

39. The method of claim 33 wherein the sheath assembly is a vascular catheter comprising at least one lumen.

40. An ultrasonic medical device for removing an occlusion comprising:
  an elongated, flexible probe having a distal end, a proximal end and a longitudinal length therebetween; and
  a horn assembly engaged to the proximal end of the elongated, flexible probe; and
  a coupling assembly that engages the horn assembly to the elongated, flexible probe,
    wherein a transfer of energy from the horn assembly to the elongated, flexible probe produces a transverse ultrasonic vibration along at least a portion of the longitudinal length of the elongated, flexible probe, producing a plurality of transverse vibration anti-nodes along at least a portion of the longitudinal length of the elongated, flexible probe.

41. The device of claim 40 providing the elongated, flexible probe that has a small cross sectional profile that allows insertion of the elongated, flexible probe into a blood vessel.

42. The device of claim 40 wherein a diameter of the elongated, flexible probe is approximately the same along the longitudinal length of the elongated, flexible probe.

43. The device of claim 40 wherein the elongated, flexible probe has a plurality of segment intervals along the longitudinal length of the elongated, flexible probe, wherein each segment interval has a different diameter.

44. The device of claim 40 wherein the elongated flexible probe vibrates in a direction transverse to at least a portion of the longitudinal length of the elongated, flexible probe.

45. The device of claim 40 wherein at least a portion of the longitudinal length of the elongated, flexible probe has a plurality of anti-nodes.

46. The device of claim 45 wherein at least a portion of the longitudinal length of the elongated, flexible probe has an at least one anti-node that is a point of a maximum transverse ultrasonic vibration.

47. The device of claim 40 wherein a flexibility of the elongated, flexible probe allows the elongated, flexible probe to be inserted into a narrow interstice without damage to the elongated, flexible probe or the narrow interstice.

48. The device of claim 40 wherein the elongated, flexible probe is adapted to be inserted into a vascular introducer.

49. The device of claim 40 wherein the elongated, flexible probe is a single diameter wire with an approximately uniform cross section.

50. The device of claim 40 wherein the elongated, flexible probe is tapered along at least a portion of the longitudinal length of the elongated, flexible probe to control an amplitude of a transverse wave along at least a portion of the longitudinal length of the elongated, flexible probe.

51. The device of claim 40 wherein the elongated, flexible probe can support the transverse ultrasonic vibration along the longitudinal length of the elongated, flexible probe.

52. The device of claim 40 wherein the elongated, flexible probe comprises titanium.

53. The device of claim 40 wherein the coupling assembly comprises a releasable compressive clamp mounted externally to a collet residing in a housing assembly at a distal end of the coupling assembly wherein the collet is capable of releasably engaging the elongated, flexible probe.

54. The device of claim 53 wherein the releasable compressive clamp is capable of exerting a compressive force on the collet causing the collet to engage the elongated, flexible probe.

55. A method of removing an occlusion in an interstice of a body comprising:

engaging a coupling assembly to a proximal end of an elongated, flexible probe and a distal end of a horn assembly; and transferring energy from the horn assembly to the elongated, flexible probe; and producing a transverse ultrasonic vibration along at least a portion of a longitudinal length of the elongated, flexible probe, causing a plurality of transverse vibration anti-nodes along at least a portion of the longitudinal length of the elongated, flexible probe.

56. The method of claim 55 providing a length of the elongated, flexible probe that is inserted into the interstice of the body.

57. The method of claim 55 providing an external energy source that engages to the horn assembly at a proximal end of the horn assembly.

58. The method of claim 55 providing an energy from an external energy source that is transmitted to the horn assembly and modified by the horn assembly.

59. The method of claim 55 providing the horn assembly that transmits an energy from an external energy source to the elongated, flexible probe through the coupling assembly wherein the energy is generated from an external energy source.

60. The method of claim 55 providing the transverse ultrasonic vibration of the elongated, flexible probe that provides a plurality of anti-nodes along at least a portion of the longitudinal length of the elongated, flexible probe.

61. The method of claim 60 wherein the anti-nodes are points of maximum transverse ultrasonic vibration along at least a portion of the longitudinal length of the elongated, flexible probe.

62. The method of claim 55 providing the coupling assembly that comprises a locking nut that engages the horn assembly at the proximal end of the elongated, flexible probe.

63. The method of claim 55 providing the elongated, flexible probe that has a flexibility that allows the elongated, flexible probe to be inserted into a narrow interstice without damage to the elongated, flexible probe or the narrow interstice.

64. The method of claim 55 providing the elongated, flexible probe that is adapted to be inserted into a vascular introducer.

65. The method of claim 55 providing the elongated, flexible probe that is tapered along at least a portion of the longitudinal length of the elongated, flexible probe to control an amplitude of a transverse wave along at least a portion of the longitudinal length of the elongated, flexible probe.

66. The method of claim 55 providing the elongated, flexible probe that can support the transverse ultrasonic vibration along the longitudinal length of the elongated, flexible probe.

67. The method of claim 55 providing the coupling assembly that comprises a releasable compressive clamp mounted externally to a collet residing in a housing assembly at a distal end of the coupling assembly wherein the collet is capable of releasably engaging the elongated, flexible probe.

68. The method of claim 67 wherein the releasable compressive clamp is capable of exerting a compressive force on the collet causing the collet to engage the elongated, flexible probe.

* * * * *